US011278589B2

(12) United States Patent
Wolf et al.

(10) Patent No.: US 11,278,589 B2
(45) Date of Patent: Mar. 22, 2022

(54) USE OF A CYCLIC TRIPEPTIDE FOR IMPROVING CELLULAR ENERGY METABOLISM

(71) Applicants: ASSISTANCE PUBLIQUE—HOPITAUX DE PARIS, Paris (FR); UNIVERSITE DE PARIS, Paris (FR); INSTITUT NATIONAL DE LA SANTE ET DE LA RECHERCHE MÉDICALE (INSERM, Paris (FR); CENTRE NATIONAL DE LA RECHERCHE SCIENTIFIQUE, Paris (FR)

(72) Inventors: Jean-Philippe Wolf, Paris (FR); Anne Lombes, Paris (FR); Morgane Bomsel, Paris (FR)

(73) Assignees: ASSISTANCE PUBLIQUE—HOPITAUX DE PARIS, Paris (FR); UNIVERSITE DE PARIS, Paris (FR); INSTITUT NATIONAL DE LA SANTE ET DE LA RECHERCHE MÉDICALE (INSERM), Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/761,825

(22) PCT Filed: Sep. 21, 2016

(86) PCT No.: PCT/EP2016/072476
§ 371 (c)(1),
(2) Date: Mar. 21, 2018

(87) PCT Pub. No.: WO2017/050854
PCT Pub. Date: Mar. 30, 2017

(65) Prior Publication Data
US 2018/0264075 A1 Sep. 20, 2018

(30) Foreign Application Priority Data
Sep. 21, 2015 (FR) .................................... 1558899

(51) Int. Cl.
*A61K 38/12* (2006.01)
*B63B 21/00* (2006.01)
*A61K 8/64* (2006.01)
*C07K 14/705* (2006.01)
*C07K 7/64* (2006.01)
*C07K 5/087* (2006.01)
*A61P 15/08* (2006.01)
*A61K 9/00* (2006.01)

(52) U.S. Cl.
CPC ................ *A61K 38/12* (2013.01); *A61K 8/64* (2013.01); *A61K 9/0014* (2013.01); *A61K 9/0048* (2013.01); *A61P 15/08* (2018.01); *B63B 21/00* (2013.01); *C07K 5/0812* (2013.01); *C07K 7/64* (2013.01); *C07K 14/705* (2013.01); *B63B 2021/004* (2013.01)

(58) Field of Classification Search
None
See application file for complete search history.

(56) References Cited

U.S. PATENT DOCUMENTS

2007/0082839 A1 4/2007 Bomsel
2015/0051152 A1 2/2015 Bomsel et al.

OTHER PUBLICATIONS

A. Ziyyat et al.: "Cyclic FEE peptide increases human gamete fusion and potentiates its RGD-induces inhibition", Human Reproduction, vol. 20, No. 12, Aug. 11, 2005 (Aug. 11, 2005), pp. 3452-3458, XP055291445, GB.
R. Rotival et al: "Comprehensive determination of the cyclic FEE peptide chemical stability in solution", Journal of Pharmaceutical and Biomedical Analysis, vol. 89, Oct. 29, 2013 (Oct. 29, 2013), pp. 50-55, XP055291515, US.
Barraud-Lange V et al: "Cyclic QDE peptide increases fertilization rates and provides healthy pups in mouse", Fertility and Sterility, Elsevier Science Inc, New York, NY, USA, vol. 91, No. 5, May 1, 2009 (May 1, 2009), pp. 2110-2115, XP026057612.
Vautier et al., "Infertilité masculine: la recherche progresse", Aug. 26, 2015, https://www.allodocteurs.fr/grossesse-enfant/procreation/fertilite-infertilite/infertilite-masculine-la-recherche-progresse_9214.html, pp. 1-3, with English translation.
Jean-philippe Wolf, "Improvement of IVF fertilization rates, by the cyclic tripeptide FEE—prospective randomized study", clinicaltrials.gov, Jun. 12, 2014, pp. 1-6.

*Primary Examiner* — Thomas S Heard
(74) *Attorney, Agent, or Firm* — MH2 Technology Law Group, LLP

(57) ABSTRACT

The present invention relates to the use of a cyclic peptide comprising the tripeptide reproducing a binding site of fertilin beta to the oocyte integrin, for improving cellular energy metabolism. More particularly, the invention concerns the use of a cyclic peptide comprising the tripeptide FEEc for stimulating the energy metabolism of gametes or embryonic cells in the context of medically assisted procreation (MAP) protocols, in particular promoting the in vitro maturation of the oocyte, the fertilization rate and the birth rate.

Figure 1:
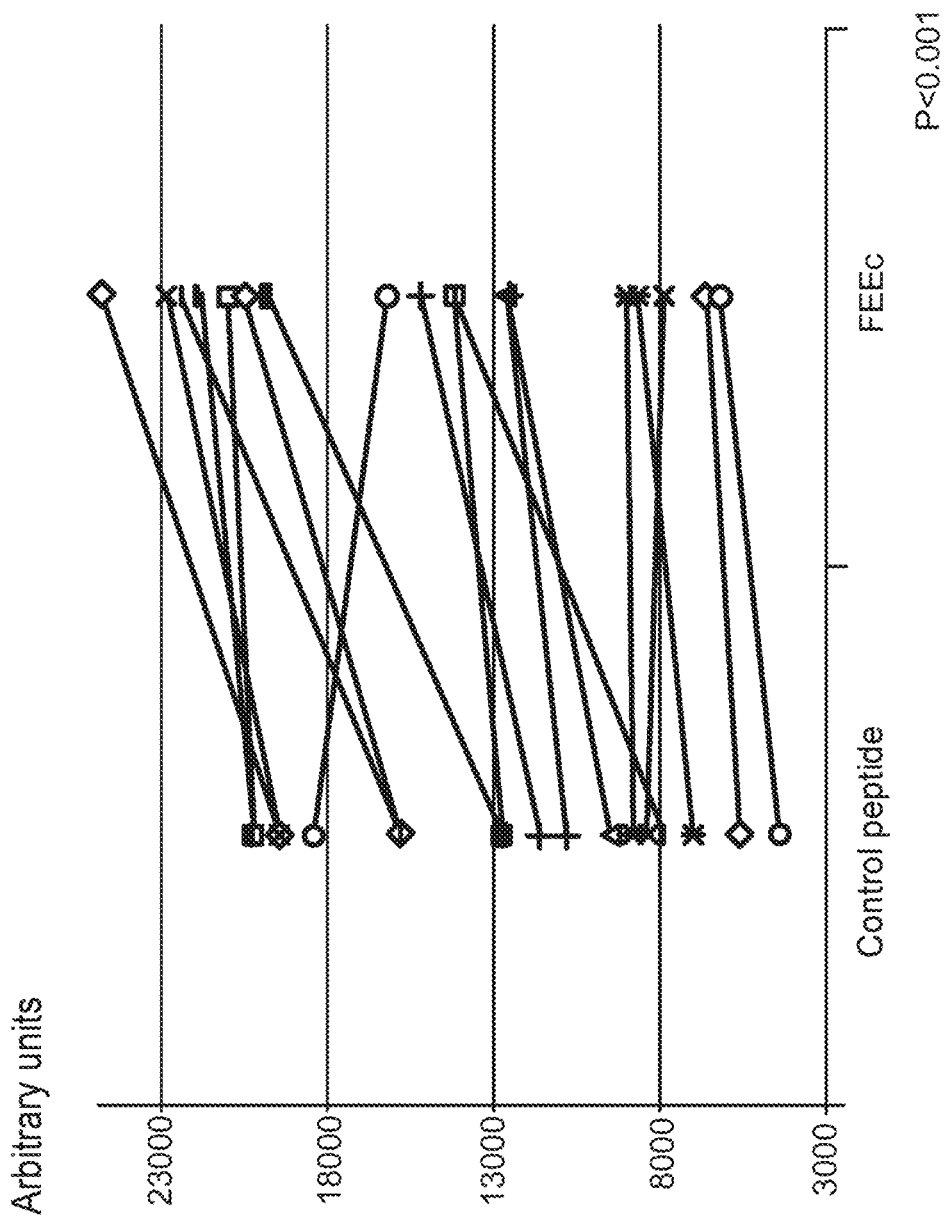

9 Claims, 14 Drawing Sheets
Specification includes a Sequence Listing.

SEQUENCE LISTING

```
<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: Cyclic Tripeptide

<400> SEQUENCE: 1

Cys Ser Phe Glu Glu Cys
```

```
<210> SEQ ID NO 2
<211> LENGTH: 30
<212> TYPE: PRT
<213> ORGANISM: Homo sapiens

<400> SEQUENCE: 2

Cys Leu Phe Met Ser Lys Glu Arg Met Cys Arg Pro Ser Phe Glu Glu
1               5                   10                  15

Cys Asp Leu Pro Glu Tyr Cys Asn Gly Ser Ser Ala Ser Cys
            20                  25                  30

<210> SEQ ID NO 3
<211> LENGTH: 30
<212> TYPE: PRT
<213> ORGANISM: Mus musculus

<400> SEQUENCE: 3

Cys Lys Leu Lys Arg Lys Gly Glu Val Cys Arg Leu Ala Gln Asp Glu
1               5                   10                  15

Cys Asp Val Thr Glu Tyr Cys Asn Gly Thr Ser Glu Val Cys
            20                  25                  30

<210> SEQ ID NO 4
<211> LENGTH: 30
<212> TYPE: PRT
<213> ORGANISM: Cavia porcellus

<400> SEQUENCE: 4

Cys Glu Phe Lys Thr Lys Gly Glu Val Cys Arg Glu Ser Thr Asp Glu
1               5                   10                  15

Cys Asp Leu Pro Glu Tyr Cys Asn Gly Ser Ser Gly Ala Cys
            20                  25                  30

<210> SEQ ID NO 5
<211> LENGTH: 30
<212> TYPE: PRT
<213> ORGANISM: Oryctolagus cuniculus

<400> SEQUENCE: 5

Cys Thr Phe Lys Glu Arg Gly Gln Ser Cys Arg Pro Pro Val Gly Glu
1               5                   10                  15

Cys Asp Leu Phe Glu Tyr Cys Asn Gly Thr Ser Ala Leu Cys
            20                  25                  30

<210> SEQ ID NO 6
<211> LENGTH: 30
<212> TYPE: PRT
<213> ORGANISM: Macaca nigra

<400> SEQUENCE: 6

Cys Leu Phe Met Ser Gln Glu Arg Cys Cys Arg Pro Ser Phe Asp Glu
1               5                   10                  15

Cys Asp Leu Pro Glu Tyr Cys Asn Gly Thr Ser Ala Ser Cys
            20                  25                  30

<210> SEQ ID NO 7
<211> LENGTH: 30
<212> TYPE: PRT
<213> ORGANISM: Bos taurus

<400> SEQUENCE: 7
```

```
Cys Ala Phe Ile Pro Lys Gly His Ile Cys Arg Gly Ser Thr Asp Glu
1               5                   10                  15

Cys Asp Leu His Glu Tyr Cys Asn Gly Ser Ser Ala Ala Cys
                20                  25                  30

<210> SEQ ID NO 8
<211> LENGTH: 30
<212> TYPE: PRT
<213> ORGANISM: Rattus rattus

<400> SEQUENCE: 8

Cys Asn Leu Lys Ala Lys Gly Glu Leu Cys Arg Pro Ala Asn Gln Glu
1               5                   10                  15

Cys Asp Val Thr Glu Tyr Cys Asn Gly Thr Ser Glu Val Cys
                20                  25                  30

<210> SEQ ID NO 9
<211> LENGTH: 30
<212> TYPE: PRT
<213> ORGANISM: Sus scrofa

<400> SEQUENCE: 9

Cys Ser Phe Met Ala Lys Gly Gln Thr Cys Arg Leu Thr Leu Asp Glu
1               5                   10                  15

Cys Asp Leu Leu Glu Tyr Cys Asn Gly Ser Ser Ala Ala Cys
                20                  25                  30
```

USE OF A CYCLIC TRIPEPTIDE FOR IMPROVING CELLULAR ENERGY METABOLISM

SEQUENCE LISTING

The instant application contains a Sequence Listing which has been submitted electronically in ASCII format and is hereby incorporated by reference in its entirety. Said ASCII copy, created on Jun. 24, 2020, is named 0177_0150_ST25 Amended SL.txt and is 2,985 bytes in size.

The present invention relates to the field of medically assisted procreation (MAP) and more particularly to all the medical, veterinary or other applications in which a stimulation of the mitochrondrial activity, or more generally the energy activity, of cells is desired, in particular during protocols comprising a step of cell culture or of cell maintenance ex vivo.

More than 15% of couples have recourse to medically assisted procreation during their genital lifespan. When the sperm is impaired, it is common to resort to microinjection techniques in order to obtain fertilizations. This technique is very invasive for the oocyte. Moreover, during in vitro fertilization (IVF) with normal sperm, 3 to 5% of unexplained fertilization failures are regularly encountered.

In a prior patent application (WO 2005/051799 A2), the team of the inventors described a cyclic tripeptide (Phe, Ac Glu, Ac Glu) of formula C-S-F-E-E-C(SEQ ID No. 1) with a cyclization linkage between the two end cysteines (FEEc), and also its action increasing the fertilization capacities of human gametes. Equivalents of the molecule exist in the various animal species, which have the same properties and are also described in said document.

Pursuing their research, the inventors have demonstrated that the FEEc molecule has an impact on the spermatozoa (example 1 below). In particular, it improves the parameters of sperm movement, as analyzed by CASA (Computer Aided Sperm Analysis). Thus, for example, the linear speed and the amplitude of lateral tiring of the head are respectively increased by 7% and 8% ($P<0.05$ and $P<0.002$) (example 1). This results in an increase of close to 30% of the percentage of hyperactivated spermatozoa ($P<0.009$). It is these hyperactivated spermatozoa which are the fertilizing spermatozoa. In order for the spermatozoan to increase its speed of progression, it is logical to think that it increases its ATP consumption or at least that its energy metabolism is enhanced, since its movement is created by binding dynein arms to the tubules in the vicinity of the axoneme. Dyneins are ATPases. By studying the mitochondrial metabolism of spermatozoa exposed to FEEc, the inventors have put forward the hypothesis that said FEEc induces an increase in the mitochondrial membrane potential, attesting either to an increase in ATP synthesis by the mitochondria, or to a reduced consumption. Thus, FEEc improves the mitochondrial energy metabolism or more generally the cellular energy metabolism of spermatozoa, either by improving ATP production, or by rationing its use by the cell.

The present invention therefore relates, in general, to the use of a cyclic peptide comprising the tripeptide reproducing a binding site of fertilin beta to the oocyte integrin or of a tripeptide of formula EEP (SEQ ID No. 2), for use thereof as a medicament for improving mitochondrial activity or more generally for improving cellular energy metabolism. The applications of such a peptide are illustrated herein on two different cell types, namely the spermatozoan and the oocyte, and on the development of a multicellular organism which is an embryo. The results presented in the experimental section support the fact of being able to use this peptide in other applications in which an improvement in cellular energy metabolism is desired. In particular, this peptide may be of use for improving the yield of cell cultures, in particular of lymphocytes. In one particular embodiment, the peptide is vectorized, that is to say administered in combination with an agent, a molecule, a composition or any other type of vector which facilitates its entry into the cells. More generally, the vectorization serves to modulate and control the distribution of an active ingredient to a target by combining it with a vector.

In the aforementioned, the "cyclic peptide comprising the tripeptide reproducing a binding site of fertilin beta to the oocyte integrin" corresponds to the peptide described in patent application WO 2005/051799 A2 mentioned above. As mentioned in this prior application, in particular in table 1, the tripeptide varies according to species. It may be cyclized by any means known to those skilled in the art, in particular by means of two cysteine residues located on either side of the tripeptide. Generally, all the variations described in application WO 2005/051799 A2 are considered to correspond to the definition of the "cyclic peptide comprising the tripeptide forming a binding site of fertilin beta to the oocyte integrin" for the purposes of the present invention including those set forth herein as SEQ ID NOS: 2-9. To facilitate the reading of the present text, this cyclic peptide, and also the medicament containing it as active ingredient, will be denoted herein by the formula "FEEc". Those skilled in the art will completely understand that this notation also covers the forms that can be used in species other than humans, such as, for example, the TDE cyclic tripeptide which should be used in bovines.

It will be understood on reading the detailed description of the invention which follows, and also the examples, that the scope of the present invention is not limited to the medically assisted procreation applications, but that it opens up real perspectives in many other fields. Thus, the invention relates more generally to the use of the FEEc in medical or non-medical applications in which a stimulation of cellular energy metabolism is desired.

Action on Spermatozoa in Intrauterine Insemination

By improving the sperm movement parameters, FEEc is also capable of improving the pregnancy rate in intrauterine insemination (IUI). According to a first particular aspect of the invention, the FEEc is used to increase the rate of progression of spermatozoa in a medically assisted procreation (MAP) protocol. Still in the context of an MAP, the FEEc can be used to improve the spermatozoa movement parameters and to increase the level of hyperactivated spermatozoa. Thus, the use of the FEEc is particularly advantageous in an intrauterine insemination (IUI) protocol, both in human beings and in non-human mammals. During the implementation of this aspect of the invention, the spermatozoa are preferably incubated for one minute to 3 hours in the presence of from 10 to 100 μM of peptide, then washed before the intrauterine insemination.

Action on Oocyte Maturation In Vitro

The molecule is also effective on oocytes. The in vitro maturation of human oocytes blocked in the germinal vesicle goes from 37.71% to 59.30% ($P<5.7\times10^{-5}$) in the presence of FEEc (example 2). In patients 37 years old or more, this rate goes from 36.96% to 68.29% ($P<0.003$), which shows that the molecule is particularly effective in this age range. The oocytes of women from 37 to 40 years old are aneuploid in at least 50% and more generally in approximately 80% of cases because of a drop in their mitochondrial activity. The molecule is therefore capable of improving the ploidy of oocytes and by the same token that of embryos of which the developmental potential and the implantation capacity also depend on the mitochondrial activity of the oocyte that has been fertilized. The significant increase in pregnancy rates in women under the age of 37, in the context of the "fertilin" clinical study described below, shows that this beneficial effect occurs on any oocyte and in particular during the fertilization thereof and the early embryonic development. The hypothesis according to these results is that fertilin is able to improve oocyte ploidy.

The supplementation of culture media and of in vitro fertilization media, and of embryo incubation media, with the molecule therefore makes it possible to improve oocyte and embryonic maturation (in particular for women who are under the age of 30 and those who are 37 years old or more) and the fertilization rate by conventional IVF, and also by IVF with ICSI (intracytoplasmic spermatozoan injection).

The supplementation of culture media during in vitro fertilization, with or without micromanipulation, with the FEEc molecule therefore makes it possible to improve the pregnancy rate and the rate of babies born, in particular in women under the age of 37, under the experimental conditions used.

Action in Oocyte In Vitro Maturation (IVM) Protocols

The FEEc molecule is also capable of being effective in oocyte in vitro maturation protocols for preserving fertility (IVM).

In an in vitro fertilization protocol, the maturation of the oocyte is generally completed at the time of the collection of the oocytes. However, some oocytes are sometimes still immature. In addition, some women present ovarian function abnormalities or a clinical condition which makes stimulations difficult. The punctures were therefore voluntarily carried out at an immature stage for in vitro maturation. The peptide could effectively assist in this maturation (in vitro maturation for fertility preservation).

The total immature oocyte has a large nucleus called a germinal vesicle (GV). The mature oocyte is characterized by the presence of the $1^{st}$ polar globule (PG) in the perivitelline space (between the surface of the oocyte and the zona pellucida). Only the mature oocytes are fertilizable.

The inventors have demonstrated that the FEEc makes it possible to improve the maturation of oocytes in vitro. This is explained by the effect of the tripeptide on the mitochondrial activity or on the energy metabolism of the oocyte. Indeed, the mitochondrial activity or more generally the energy metabolism decreases with age, and the maturation of the oocyte comprises several highly energy-consuming steps:

germinal vesicle rupture
chromosome condensation
metaphase plate formation
spindle formation
check-point protein synthesis
telophase
PG expulsion.

In point of fact, these oocyte maturation problems which worsen with age are corrected by the microinjection of mitochondria originating from young cells (oocytes from young donors or oogonial stem cells). This reinforces the probability according to which the FEEc actually corrects the cell defect associated with mitochondrial insufficiency or more generally energy insufficiency.

According to another of its aspects, the present invention therefore relates to the use of the FEEc for improving the in vitro maturation of an oocyte. The improvement in the quality of meiosis is probably responsible for the decrease in the rate of miscarriages that is also observed in younger women, so that this aspect of the invention is also advantageous for improving the in vitro maturation of oocytes of women under the age of 37, or even under the age of 30. In the implementation of this aspect of the invention, the oocyte is incubated for a period of between 1 hour and 4 days, in particular up to 3 days or 24 hours, and in the presence of from 10 to 100 M of peptide.

Action on the Activation of the Fertilized Oocyte

The inventors have also demonstrated an increase in spermatozoan head decondensation after fertilization. This reflects an improvement in oocyte activation during fertilization. This is moreover linked to the mitochondrial activity of the oocyte.

Action on Blast Formation

The inventors have also demonstrated (in mice) that the FEEc allows an improvement in blast formation. This can also be attributed to the effect of the tripeptide on the mitochondrial activity or more generally on the metabolism of the cell. Indeed, it is known that there is no mitochondrial DNA replication during preimplantation embryogenesis. During the first week of development, the zygote (or egg) divides by successive mitoses beginning with 2 and then 4 cells, and going through the morula stage until the blastocyst stage is reached, preferentially using the mitochondria initially present in the oocyte. A mitochondrial deficiency (in terms of number or yield) can therefore be responsible for chromosomal instability of the blastomers during meiosis and mitoses, and can result in an arrest in the evolution of the zygote, of the embryo, or even of the pregnancy. This is a common cause of spontaneous miscarriage after natural fertilization or after embryo transfer during an IVF.

The present invention therefore also relates to the use of the FEEc for improving the ploidy of blastomers during the first week of zygote development. As a result, the invention relates to the use of FEEc for decreasing the number of miscarriages. The invention also relates to the use of FEEc for decreasing the risk of aneuploidy, in particular of trisomy. In the implementation of this aspect of the invention, the embryo is incubated for a period of between 24 hours and 6 or 7 days in the presence of from 10 to 100 µM of peptide.

The uses described above are particularly useful in an in vitro fertilization (IVF) protocol. In human beings, they allow women of all ages to have children by MAP with their own oocytes without recourse to the mitochondrial injections described in the literature (major effect most widely documented to date).

Decrease in the Risks of Miscarriages

The present invention also relates to the use of the FEEc for decreasing the risks of miscarriage, as was previously mentioned and is illustrated in the experimental section below.

Decrease in the Risks of Trisomy

The present invention also relates to the use of the FEEc for decreasing the risks of trisomy, or more generally of aneuploidy, during an IVF, in all women, in particular in women 35, 36, 37, 38, 39 or 40 years old and older.

Improvement in the Kinetics of Embryo Development In Vitro

The present invention also relates to the use of FEEc for improving preimplantation embryonic development in vitro. In one particular embodiment, the preimplantation development is obtained under prolonged culture conditions. The improvement in the kinetics of the embryo development makes it possible to improve the birth rate.

Action in Natural Reproduction

Although the effects of the FEEc on the oocyte and the zygote have been demonstrated by the inventors in an IVF context, it is obvious that these effects could also be obtained during natural fertilizations, for example by administration, at the time of ovulation, of FEEc vaginally, the tripeptide being coupled to means suitable for vectorizing it to the oocyte.

Action During Gamete and Embryo Cryopreservation

It has also been shown that the survival rate of cryopreserved oocytes depends, inter alia, on the mitochondrial activity thereof. It is likely that the same is true for the embryos. The FEEc peptide is therefore capable of improving the survival rate and/or the quality of cryopreserved gametes and embryos during thawing thereof.

Action on Other Cell Types

The cyclic tripeptide was produced in order to bind to the α6β1 integrin on the oocyte. It is capable of binding to the cytoplasmic membrane of various other cell types because this integrin is very ubiquitous. This molecule is therefore probably capable of increasing the energy activity of numerous cell types. It is therefore capable of multiple uses other than IVF.

Since the mode of action of the molecule probably occurs by means of the α6β1 integrin, the FEEc is capable of having effects on many other cell types. This molecule could be used to improve the yield of any cell culture.

As mentioned above, the FEEc possibly acts by means of the α6β1 integrin or of another receptor, present on numerous cell types. It can therefore be used for improving the mitochondrial activity or the energy metabolism of any cell carrying this integrin or this other receptor. An immediate application of this property is the improvement of the yield of any cell culture. The present invention therefore also relates to a method for improving the mitochondrial activity or more generally the energy activity of cells in vitro, comprising a step of bringing the cells in question into contact with the FEEc. This method can advantageously be carried out on primary cells cultured ex vivo in the perspective of being administered to a patient in the context of a cell therapy. By way of nonlimiting examples of cell cultures capable of benefiting from this method, mention may be made of skin cultures with a view to skin grafts, lymphocyte cultures with a view to cell immunotherapies, etc.

The invention relates to the use of an FEEc peptide for the purpose of promoting the ex vivo culture of all cell types expressing an FEEc receptor, in medical applications (such as cell therapy) or non-medical applications (such as the maintaining of cells in culture for experimental purposes or for protein production).

Action in the Mammalian Animal World

The molecule exhibits a species specificity. Its isoforms can be adapted for use in all domestic or non-domestic animals, including farm animals, some species of which reproduce with difficulty (racehorses, Holstein cows).

Action on Mitochondrial Pathologies and Against Aging

The properties of the FEEc as a molecule for stimulating mitochondrial activity or more generally energy metabolism can also be used in vivo in any type of pathology linked to a mitochondrial activity defect. In this respect, mention may generally be made of aging pathologies. The relationship between mitochondrial dysfunction and neurodegenerative diseases, for example, has been established by several teams. Thus, the FEEc could be used as a medicament for treating neurodegenerative diseases such as Alzheimer's disease or Parkinson's disease. A relationship between chromosome telomere length and the mitochondrial activity of the cell has also been shown. In point of fact, telomere shortening is linked to aging processes. It is therefore possible that, by stimulating the mitochondrial or energy activity of the cell, it is possible to delay the effects of the aging.

Mitochondrial diseases present a varied picture, but frequently combine ocular manifestations of the retinitis pigmentosa or ophthalmoplegia type. For the latter pathologies, a topical administration of FEEc in the eye, for example in an eye lotion, could improve the symptoms associated with mitochondrial or energy insufficiency. Another subject of the invention is therefore an eye lotion comprising a cyclic peptide comprising the tripeptide capable of forming a binding site of fertilin beta to the oocyte integrin. Such an eye lotion may comprise, in addition to the FEEc, another agent such as a thickener, an antiseptic, an antibiotic or any other compound that can be used for this type of product. The media described in application WO 2005/051799 A2 are of course excluded from the definition of the term "eye lotion" for the purposes of the present invention.

Action in Cosmetics

The present invention also relates to the use of the FEEc in a cosmetic or therapeutic composition intended for topical application. By way of examples, mention may be made of the use of the FEEc for stimulating fibroblasts for collagen production, or for stimulating hair follicles for promoting hair growth, for example for preventing or slowing down alopecia. The present invention therefore also relates to a cosmetic or dermatological composition comprising FEEc as active ingredient. The term "cosmetic or dermatological composition" is intended to mean herein a composition which, in addition to the FEEc, comprises ingredients normally used in the cosmetology field. According to the invention, the cosmetic or dermatological composition can be in any form known to those skilled in the art. It may for example be an oil-in-water, water-in-oil or water-in-silicone emulsion, a multiple emulsion, a microemulsion, a nanoemulsion, a solid emulsion, an aqueous or aqueous-alcoholic gel, a cream, a milk, a lotion, an ointment, an oil, a balm, a salve, a mask, a powder, an impregnated support, for example a transdermal patch, an aqueous or aqueous-alcoholic lotion and/or a wax, a makeup product, for example a foundation, a shampoo, a conditioner, a mask, a serum for topical application, or a hair lotion. The media described in application WO 2005/051799 A2 are of course excluded from the definition of the cosmetic or dermatological compositions for the purposes of the present invention.

According to the invention, the cosmetic or dermatological composition may for example be a face, body or hair care composition, for example face and/or body and/or hair compositions.

The following examples illustrate the invention without, however, limiting the scope thereof.

FIGURE LEGENDS

FIG. 1: Variation in the mitochondrial membrane potential in the presence of the FEEc (on the right) versus "scramble" control peptide (on the left). The increase in the membrane potential in the exposed spermatozoa in the majority of the patients should be noted.

Figure 2:
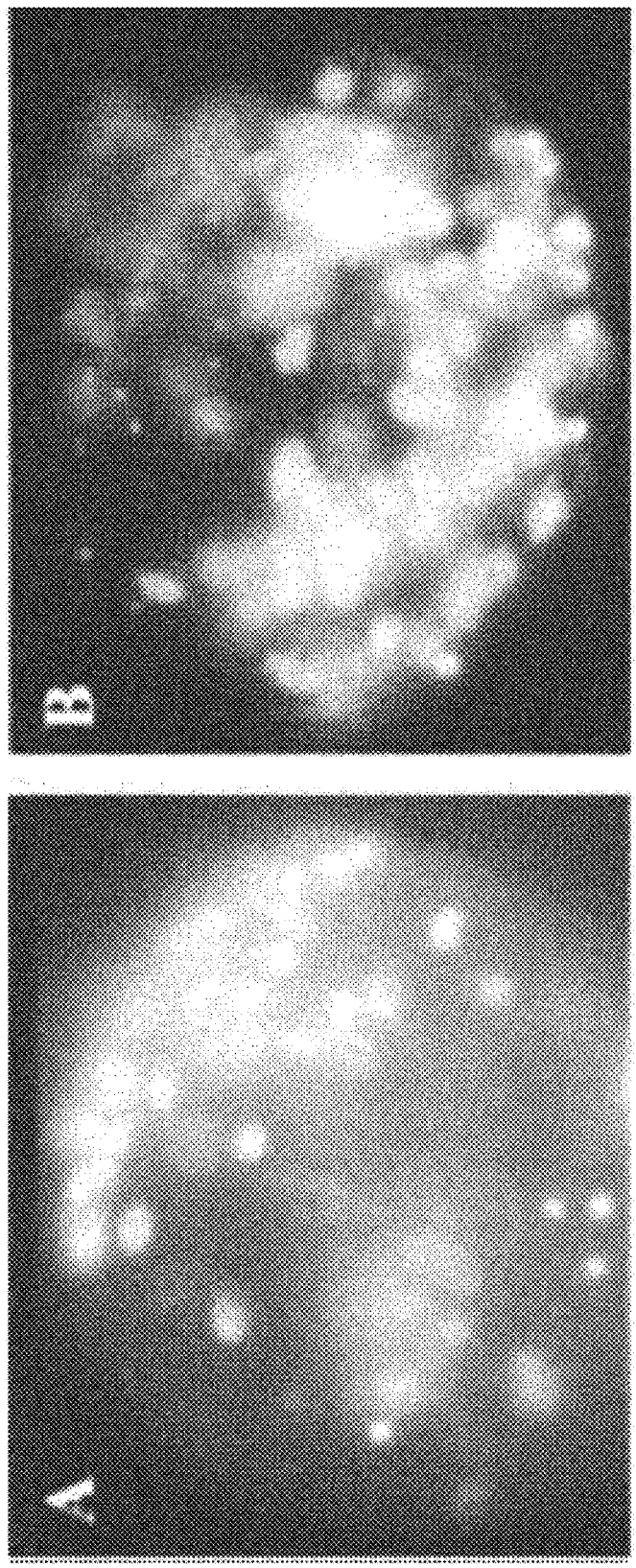

FIG. 2: Counting, after UV excitation, of the human spermatozoa fused with human oocytes with the pellucida removed, incubated in the absence (A) or in the presence of FEEc at 100 μM (B). The increase in the number of spermatozoa fused and the faster decondensation of their head should be noted.

Figure 3:
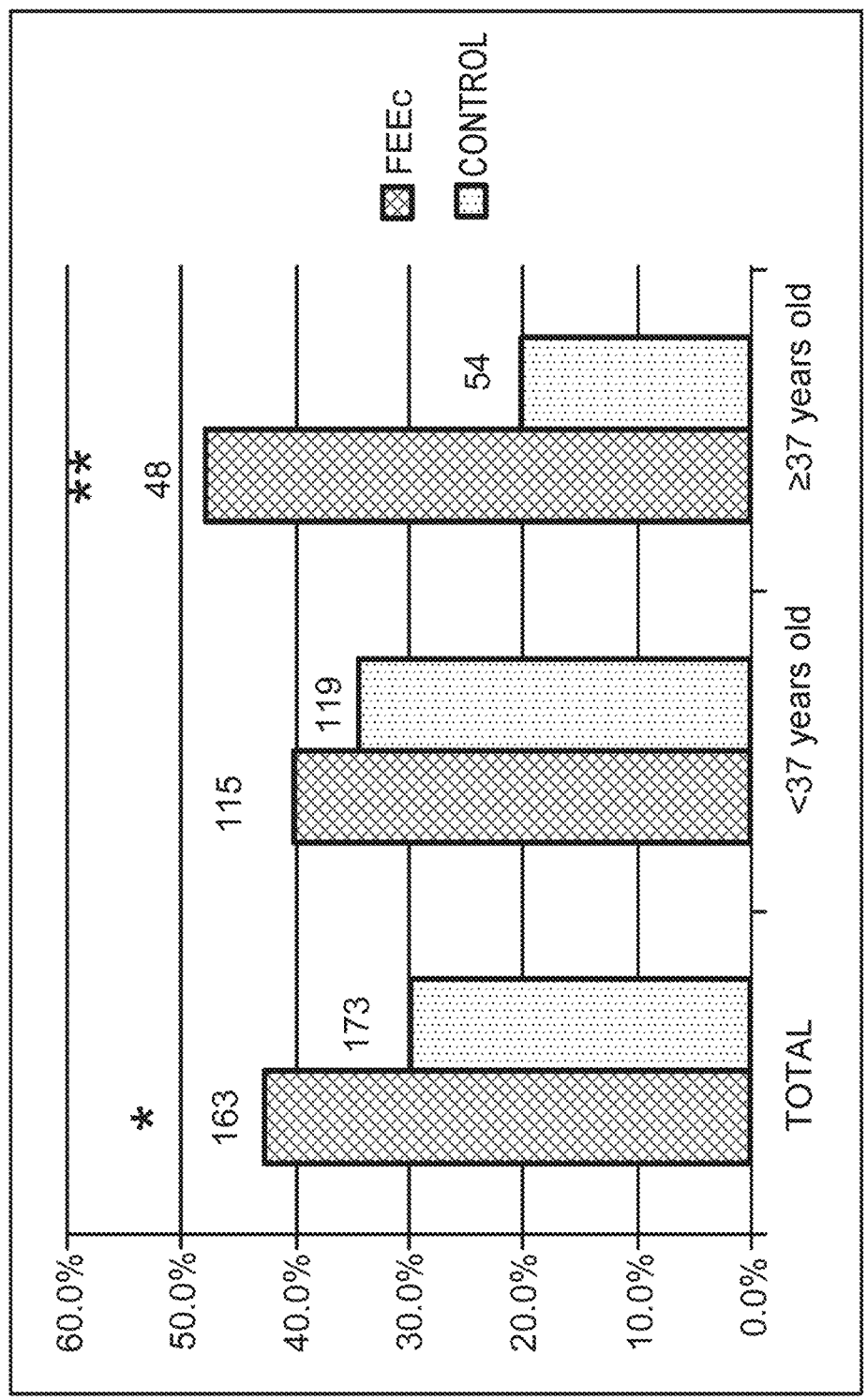

FIG. 3: Proportion of mature oocytes at D1 of in vitro maturation (IVM). Diagrammatic representation of the proportions of human oocytes in metaphase II (MII) from the GV stage after IVM in the control medium or the medium supplemented with FEEc at 100 µM. *p=0.02. **p=0.003. D1=24 h of IVM.

Figure 4:
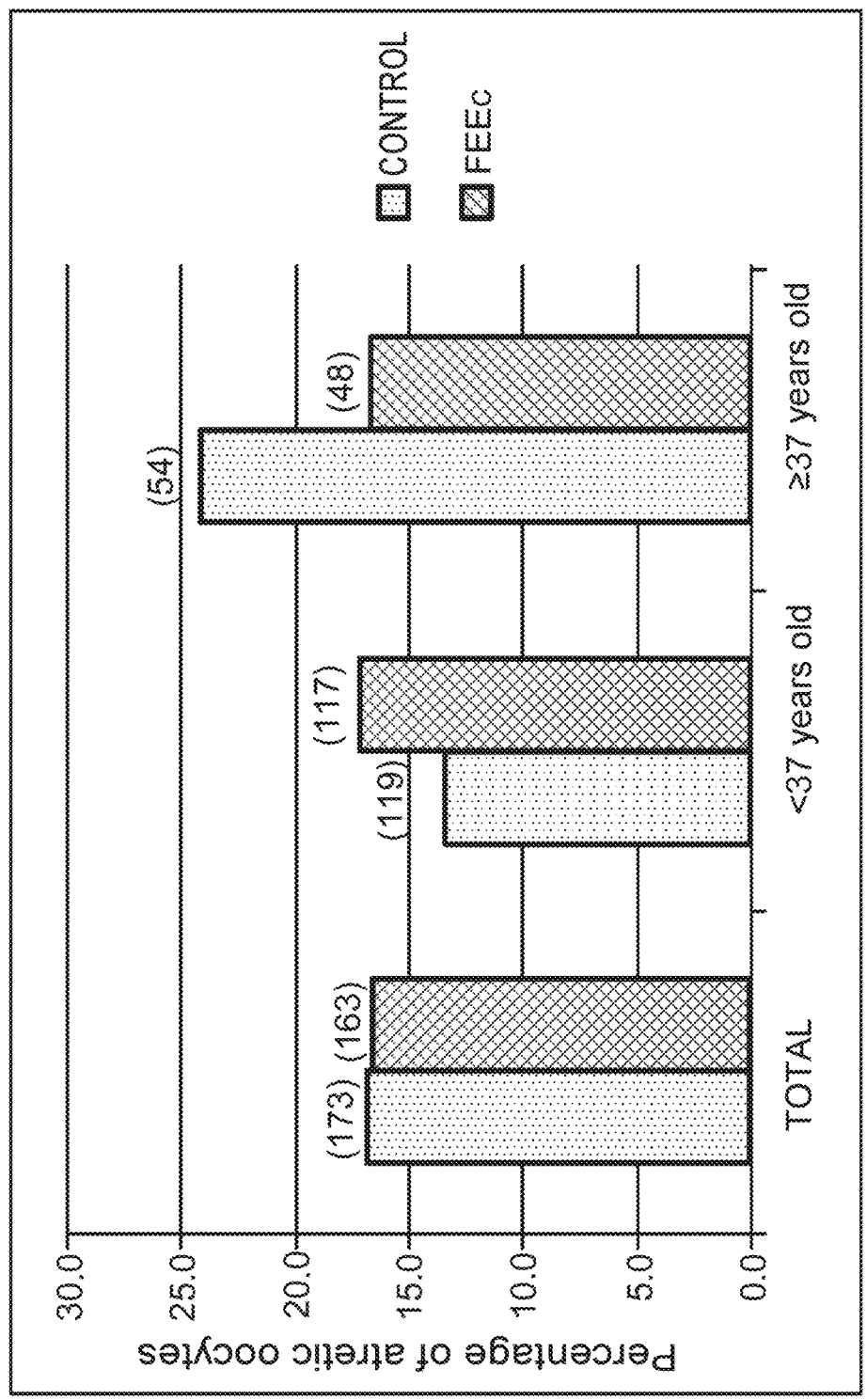

FIG. 4: Proportion of atretic oocytes at D1 of in vitro maturation (IVM). Diagrammatic representation of the proportions of atretic human oocytes. Results observed at D1 starting from the GV stage after in vitro maturation (IVM) in the control medium or the medium supplemented with FEEc at 100 µM. D1=24 h of IVM.

Figure 5:
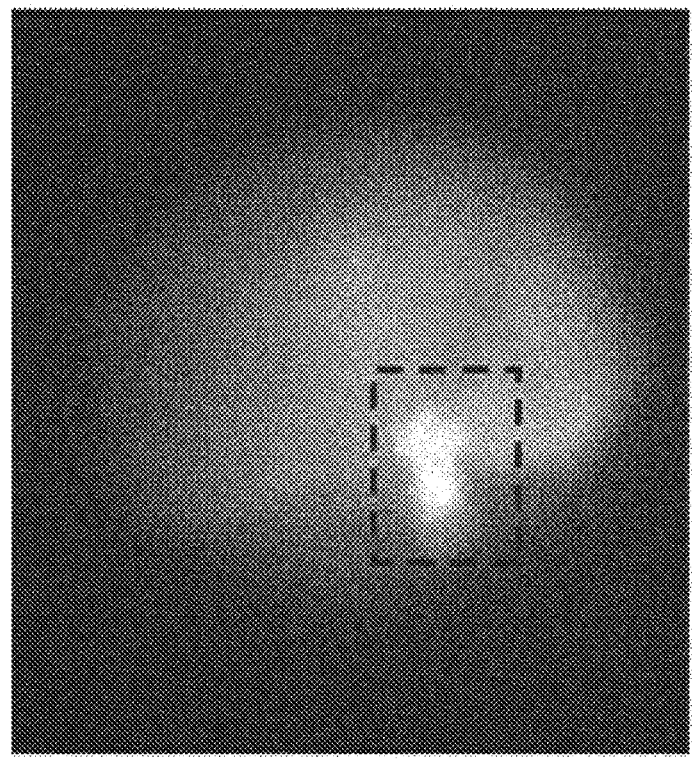
Figure 5:

FIG. 5: Labelling of the meiotic spindle obtained on a human oocyte in MII after IVM in the standard medium (24 h). Labelling of the spindle with an anti-α-tubulin antibody and of the chromosomes with DAPI. Image obtained on a confocal microscope. A: whole oocyte. B: magnification of the metaphase plate.

Figure 6:
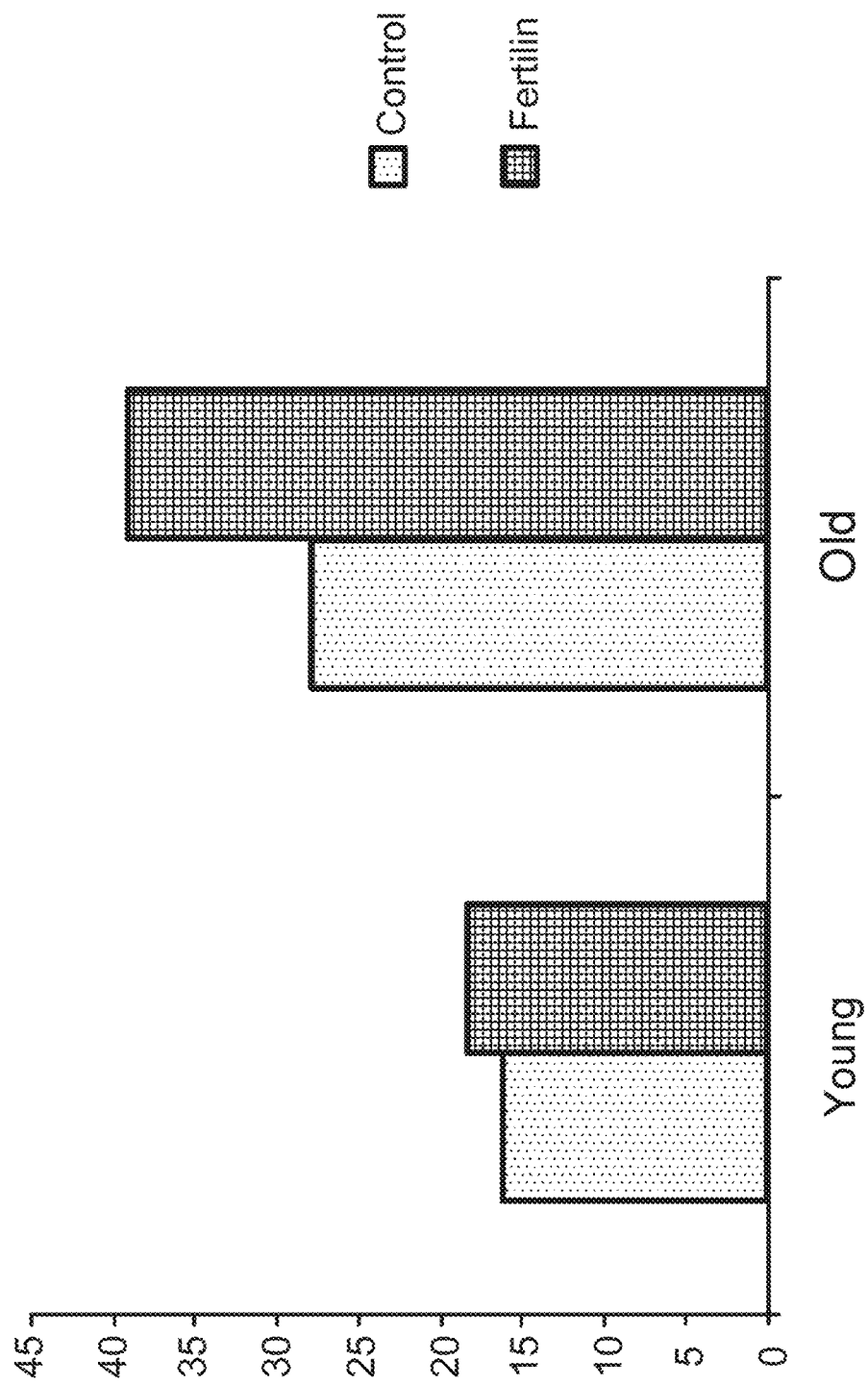

FIG. 6: Comparison of the fertilization rate at D1 between the young and old mice, in the presence or in the absence of fertilin, which corresponds to the QDEc peptide.
Young: 7-week-old B6CBAF1 mice; old: 7-month-old B6CBAF1 mice.

Figure 7:
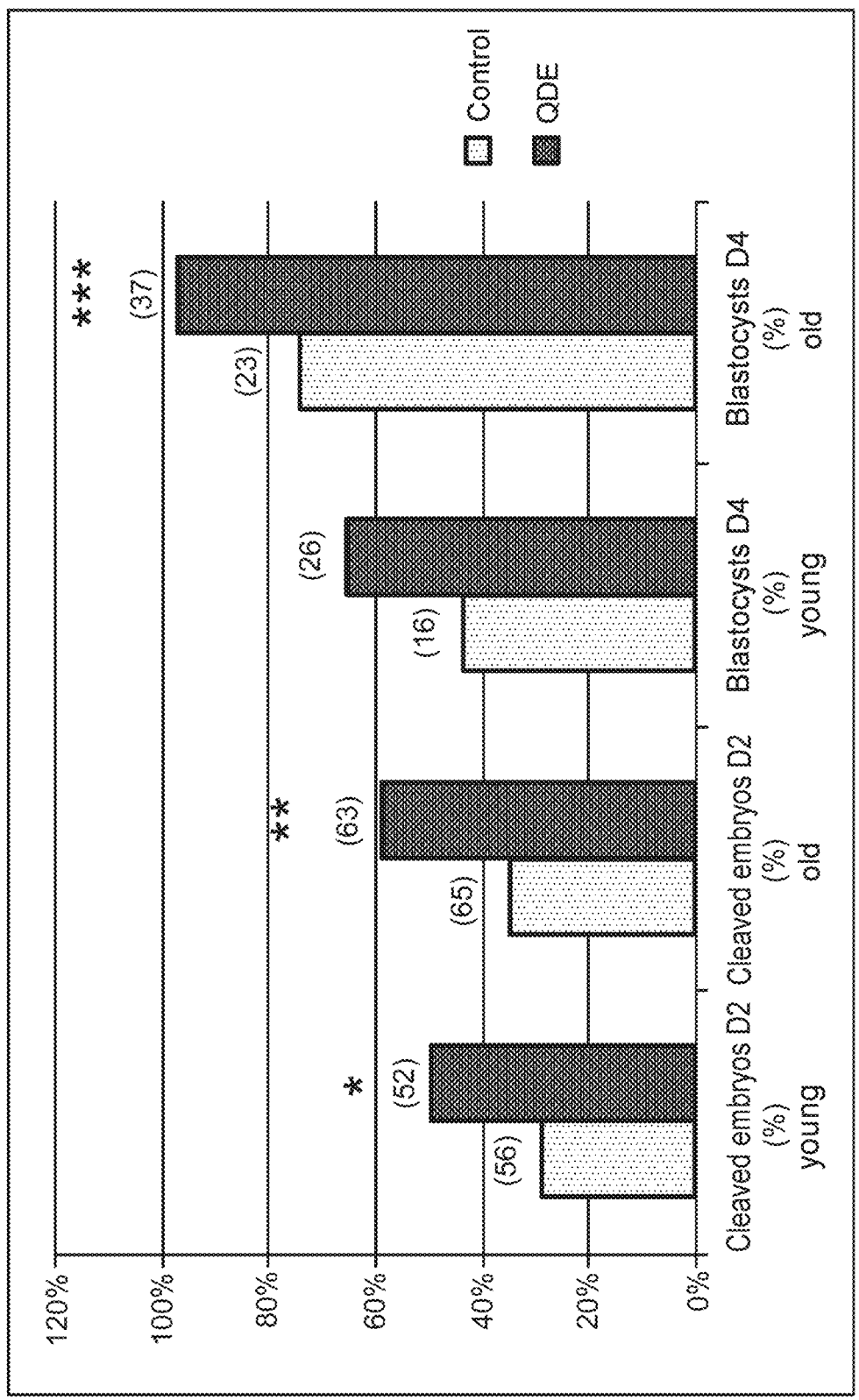

FIG. 7: Comparison of the average percentages of cleaved embryos at D2 and at D4 between the young and old mice, in the presence or absence of the QDEc peptide.
Young: 7-week-old B6CBAF1 mice (n=108 oocytes, 56 controls, 52 QDEc); old: 7-month-old B6CBAF1 mice (n=128 oocytes, 65 controls, 63 QDEc); *p=0.02, p=0.008, *p=0.01.

Figure 8:
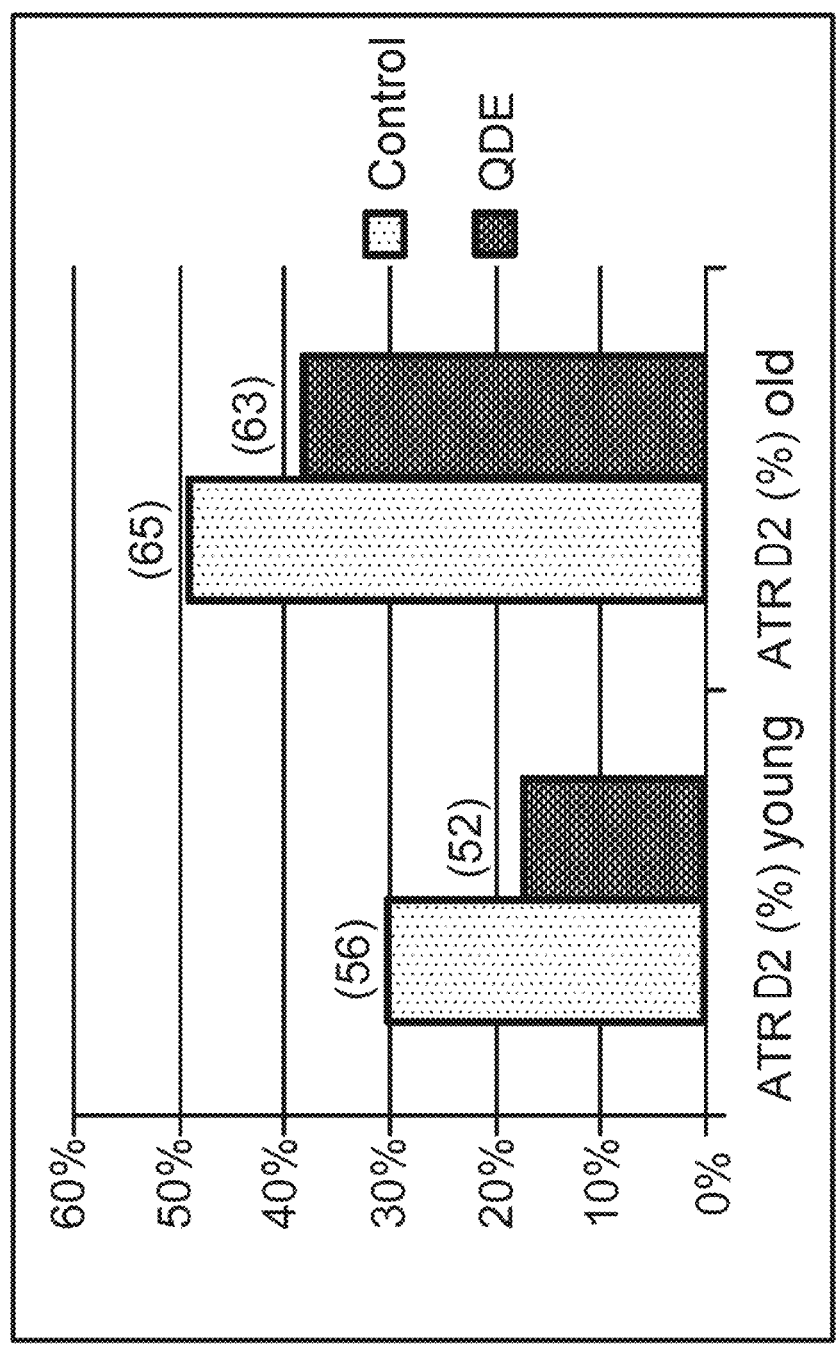

FIG. 8: Comparison of the average percentages of atresia (ATR) at D2 between the young and old mice, in the presence or absence of the QDEc peptide.
Young: 7-week-old B6CBAF1 mice (n=108 oocytes, 56 controls, 52 QDEc); old: 7-month-old B6CBAF1 mice (n=128 oocytes, 65 controls, 63 QDEc).

Figure 9:
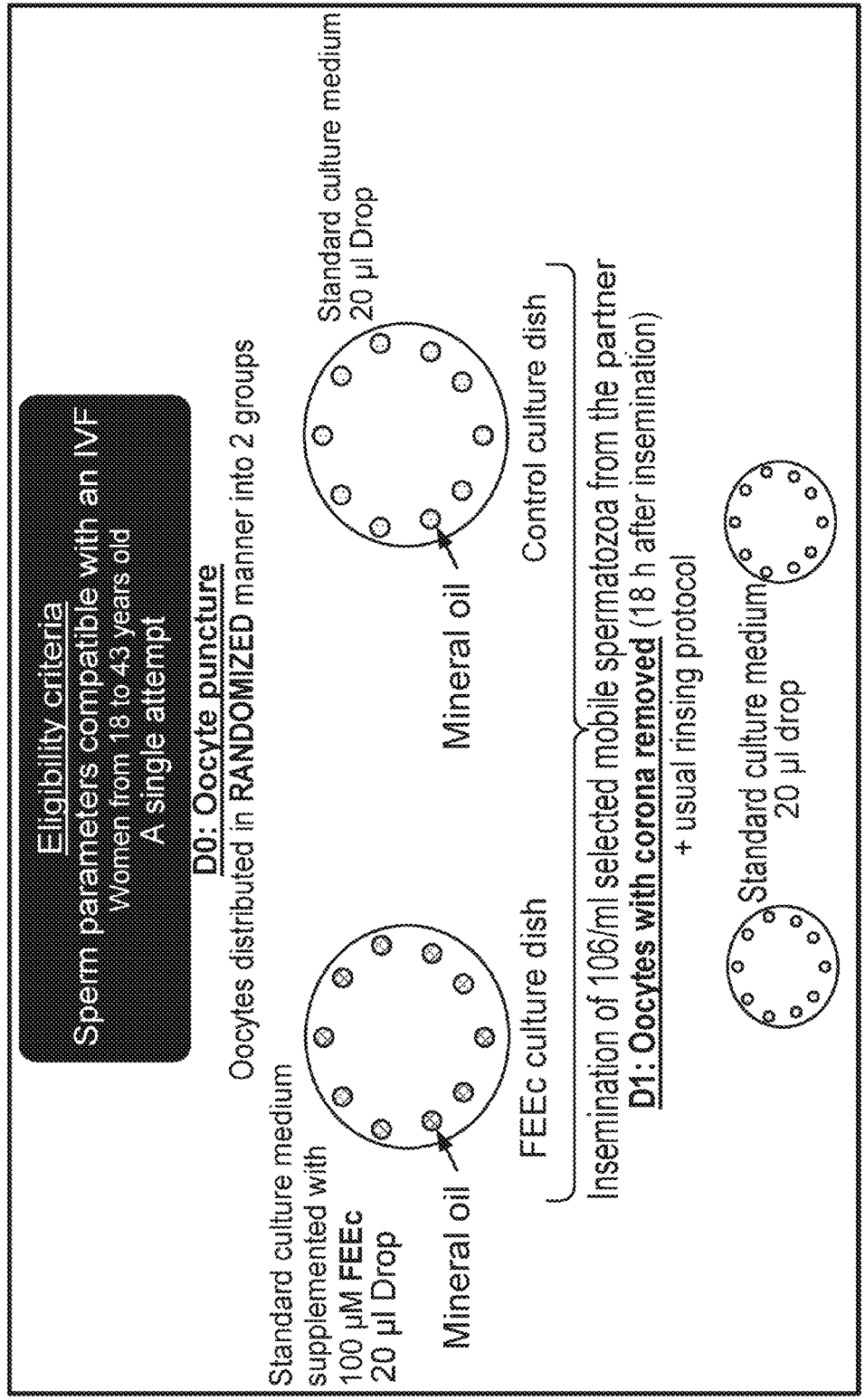

FIG. 9: Diagrammatic representation of the methodology of the clinical study carried out in example 5.

Figure 10:
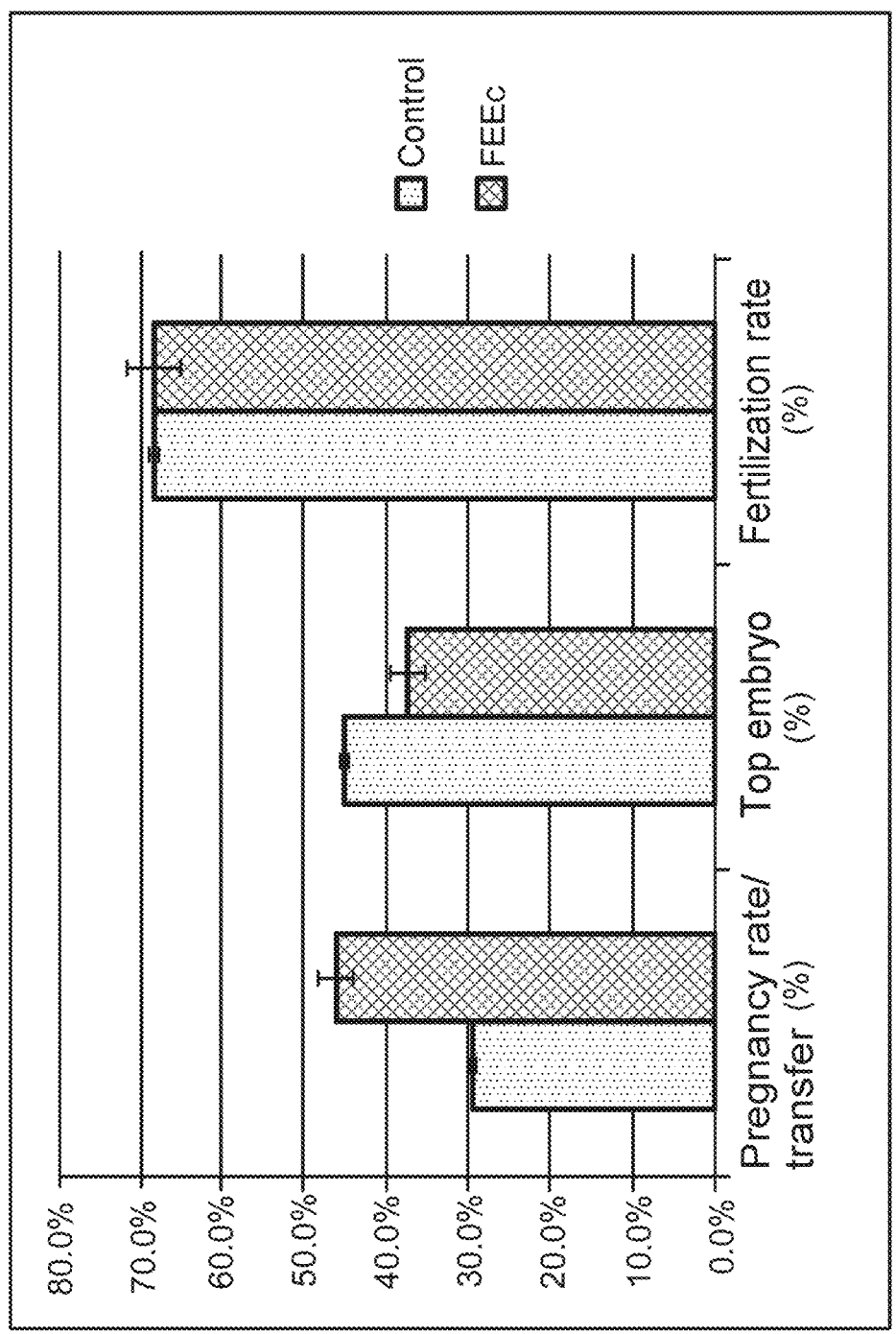

FIG. 10: Preliminary results of the criteria for main and secondary judgement in the context of the clinical study. Pregnancy rate by fresh or frozen embryo by transfer (control group, n=17 transfers/FEEc group, n=13 transfers). "Top embryo" percentage (control group, n=75 cleaved embryos/FEEc group, n=72). Fertilization rate (control group, n=259 MII/FEEc group, n=246 MII)

Figure 11:
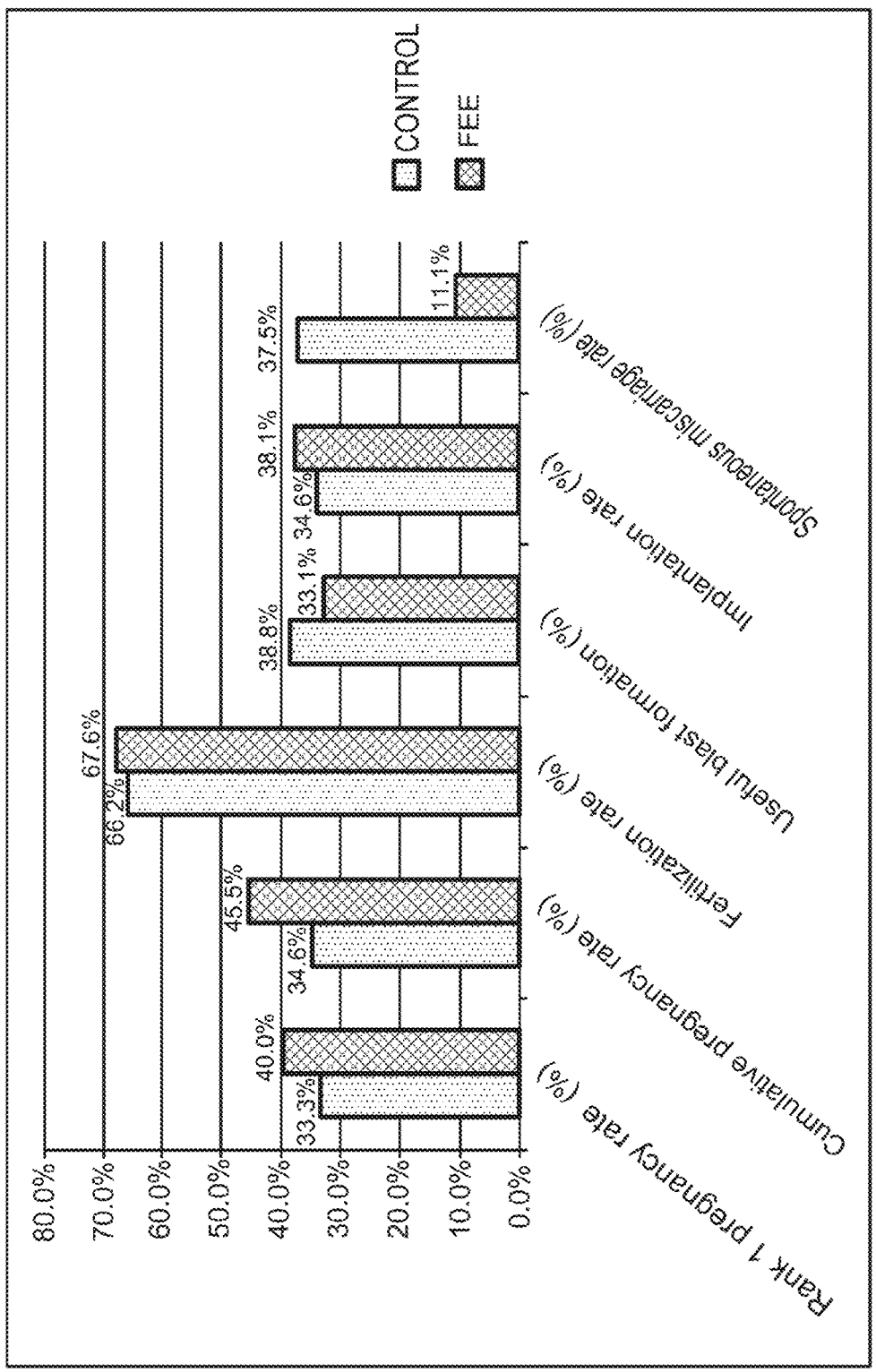

FIG. 11: Pregnancy rates obtained in the context of the clinical study.

Figure 12:
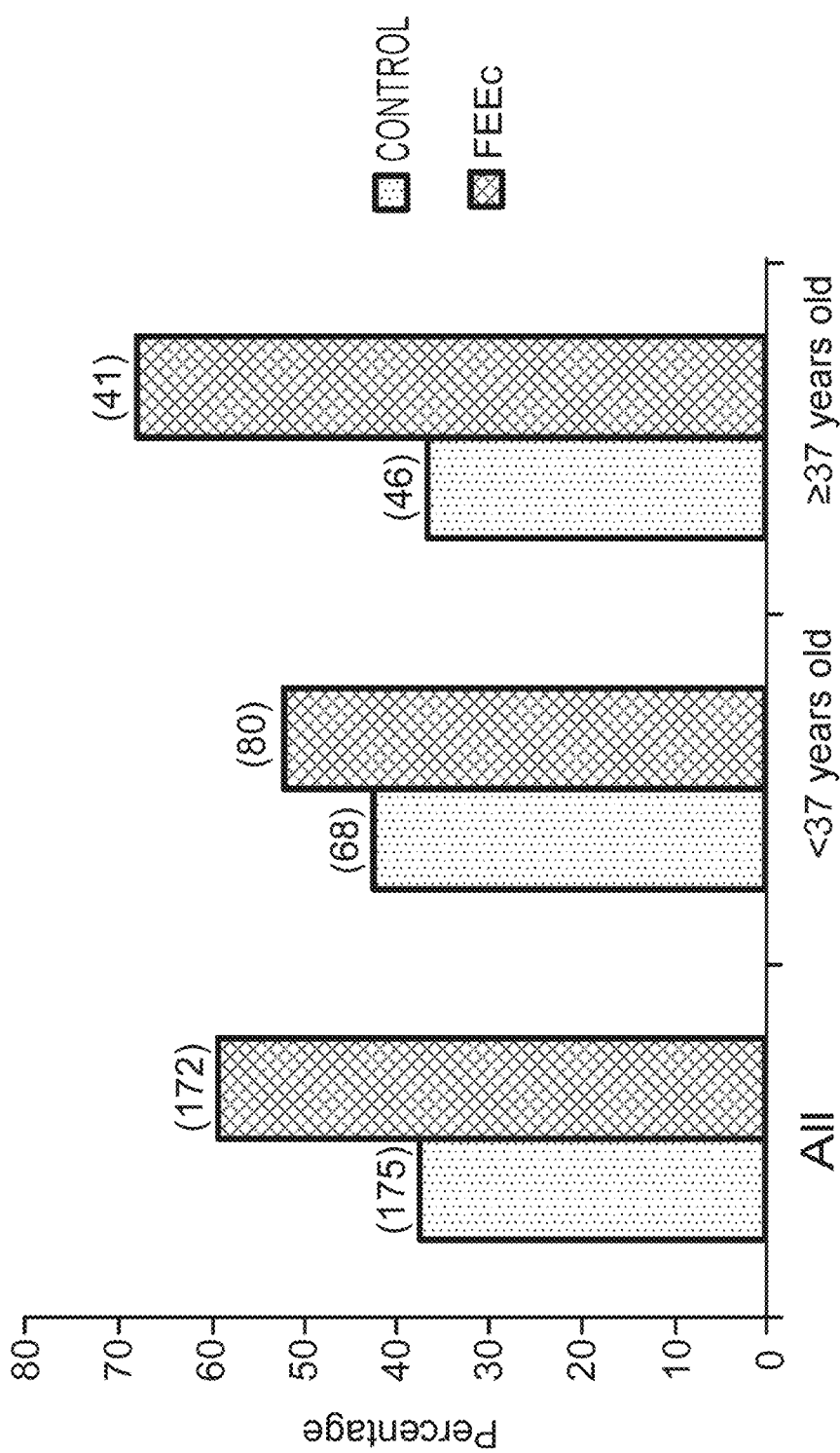

FIG. 12: Improvement in the rate of maturation of oocytes blocked in GV after incubation in the presence of the FEEc. This study was carried out by taking into consideration one oocyte per woman and by incubating said oocyte in the presence of the FEEc or of the control peptide.

Figure 13:
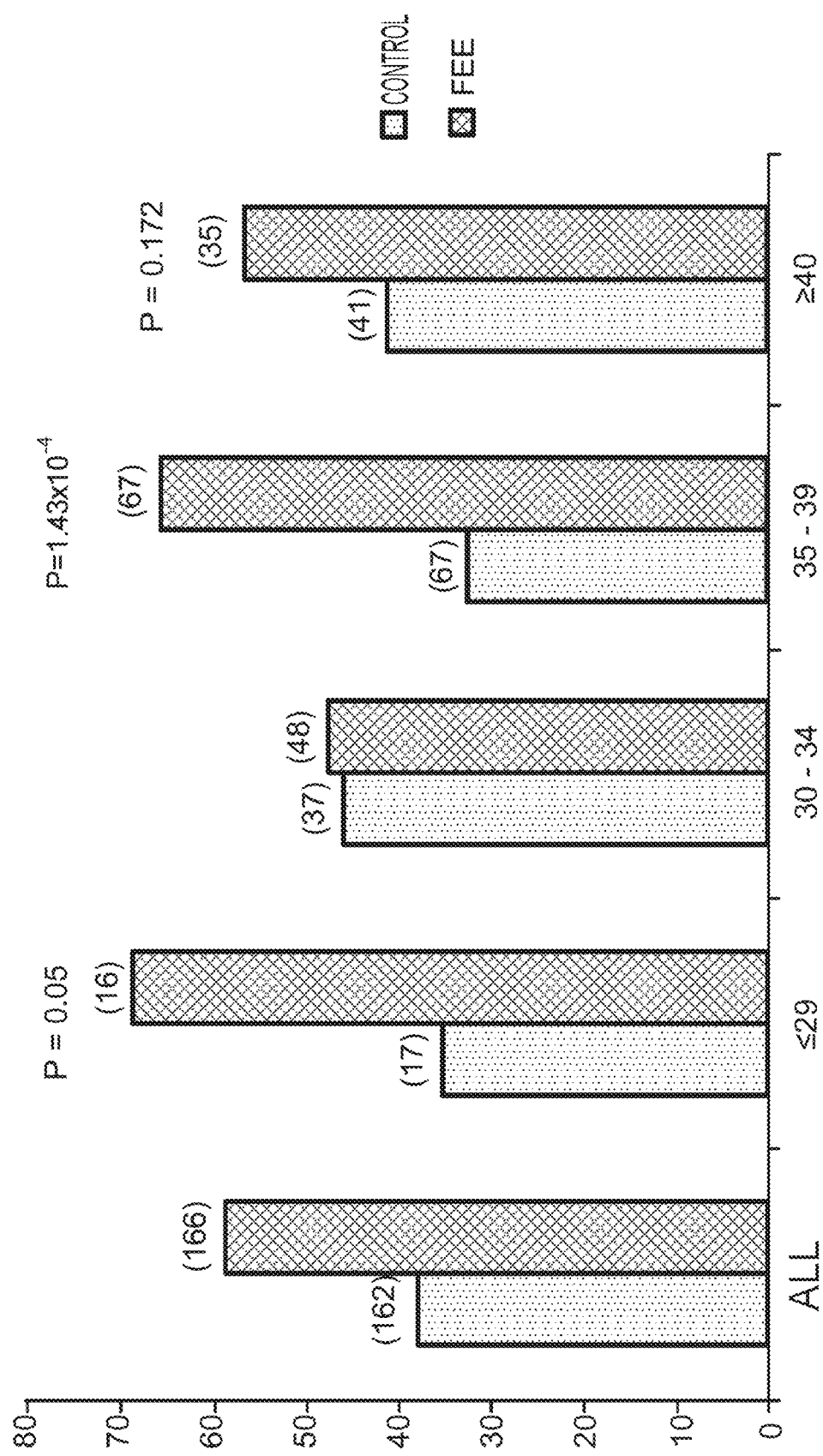

FIG. 13: Effects of FEEc on the maturation of human oocytes blocked in GV per age range.

Figure 14:
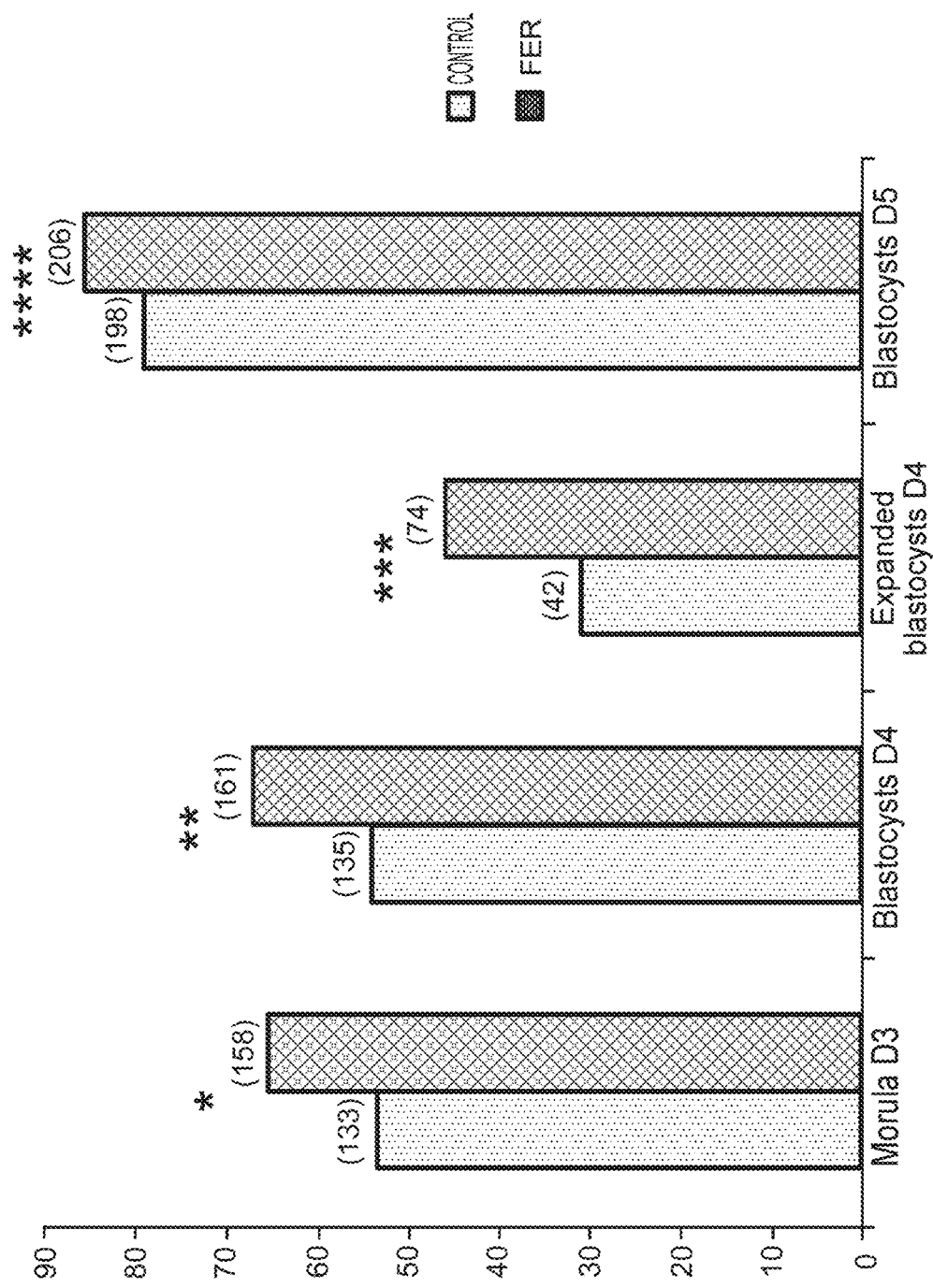

FIG. 14: Stimulation of the pre-implantation embryonic development in young mice with QDEc (*P<0.00532; P<0.00374; *P<0.00913; ****P<0.068; ( ) number of embryos).

MATERIALS AND METHODS

The experimental examples present below were obtained using the following materials and methods:
Observation of the Sperm Movement Parameters The sperms studied were each divided into 2 aliquots, one of which was incubated with the FEEc and other of which was incubated with a "scramble" peptide containing the same amino acids but in a random order. The inventors incubated, for 3 h at 37° C., spermatozoa from human beings in the presence of 100 µM of the FEEc peptide or of the scramble peptide and then observed the sperm movement parameters according to an automated analysis (Computed Assisted Sperm Analysis, CASA).

The sperm parameters tested are the following: smoothed VAP, VSL, VCL and ALH. They correspond respectively to the average path velocity, the straight line velocity, the curvilinear velocity and the lateral head displacement. The study showed a significant increase in the percentage of hyperactivated spermatozoa (according to the criteria of Mortimer et al.). This can explain the increase in fertilization rates observed in the presence of the peptide.
Measurement of the Mitochondrial Membrane Potential The inventors incubated, for 3 h at 37° C., spermatozoa from human beings in the presence either of the FEEc peptide, or of the "scramble" peptide which comprises the same amino acids in a random order and thus constitutes the control group. After washing, the spermatozoa are labelled using a lipophilic fluorescent dye, DIOC6.

The mitochondrial membrane potential (proton gradient at the level of the mitochondrial inner membrane) was then measured by flow cytometry. It is found to be increased in the spermatozoa after exposure to FEEc.
Measurement of the Fertilization Index Human oocytes with the pellucida removed were incubated with human spermatozoa in the absence or presence of FEEc at 100 µM. The fused spermatozoa were counted after UV excitation. The spermatozoa were considered to be fused when the nucleus was labelled with Hoechst 33342. Furthermore, the heads of the spermatozoa having penetrated the oocyte in the presence of the FEEc peptide are not only greater in number but also have a blurred appearance attesting to the decondensation of their sperm head. This decondensation is one of the first steps of oocyte activation after penetration of the spermatozoan. It can therefore be concluded from this that not only does the FEEc improve the fertilizing ability of the spermatozoan, but it also activates the fertilized oocyte.
Collection of Human Oocytes with a View to In Vitro Maturation (IVM)

Immature human oocytes given to research were collected from the in vitro fertilization (IVF) laboratory of the Medically Assisted Procreation (MAP) Center of the Cochin hospital (Paris, France). Two hours after the oocyte puncture, the oocytes intended to be microinjected had their corona removed with hyaluronidase (Origio, Limonest, France). After observation under an inverted microscope (Hoffman), the immature oocytes at the germinal vesicle (GV) stage were retained for the remainder of the experiments.
In Vitro Maturation (IVM) of Immature Human Oocytes The immature human oocytes at the GV stage were randomized, either in the control culture medium (Global, JCD, La Mulatière, France) (n=203) or in the same medium supplemented with 100 µM of FEEc (n=193). The immature human oocytes were categorized in two groups: those belonging to women under the age of 37 and those belonging to women aged 37 and over. On the day of the follicular puncture, the two groups of oocytes at the GV stage were incubated in 20 µl drops covered with oil, and maintained at 37° C. under 5% $CO_2$ so as to be observed under an inverted microscope (Hoffman) at D1 (24 h of incubation) and D2 (48 h of incubation). The oocytes were categorized as metaphase II ($1^{st}$ polar globule in the perivitelline space), germinal vesicle (GV), metaphase I (rupture of the germinal vesicle without expulsion of the polar globule) or atretic.

Collection of Murine Oocytes with a View to In Vitro Maturation (IVM)

B6CBAF1 females (between 5 and 8 weeks old) supplied by the Charles River laboratory (L'Arbresle, France) were stimulated by injection of PMSG (Pregnant Mare Serum Gonadotrophin) at 10 IU (Sigma-Aldrich, Saint-Quentin Fallavier, France) without triggering ovulation. The immature oocytes were collected from the ovaries 48 h after the latter injection, then had their cumulus removed by means of hyaluronidase and were washed three times in M2 culture medium. Only the oocytes categorized as GV were retained for the remainder of the experiments.

In Vitro Maturation (IVM) of the Immature Mouse Oocytes

The mouse oocytes were incubated in a manner randomized between, on the one hand, the standard medium and, on the other hand, the medium supplemented with 100 μM QDEc. The culture dishes were prepared the day before and incubated at 37° C. under 5% $CO_2$. The oocytes were observed at D0 (8 h post-sacrifice) and D1 (24 h).

Immunofluorescence

The human oocytes resulting from the IVM were fixed in 2% paraformaldehyde (PFA) for 1 h at ambient temperature and then washed in PBS containing 0.5% of BSA. The permeabilization was carried out by incubation of the oocytes in a solution containing 0.5% of BSA, 0.1% of Triton X-100, 0.05% of Tween-20 and 5% of normal goat serum. The oocytes were then washed in PBS-05% BSA before being incubated overnight in a dilution to 1/200 of anti-human α-tubulin antibody (Sigma-Aldrich) in PBS containing 0.5% of BSA. The oocytes were then incubated for 1 h in the presence of the Alexa Fluor-conjugated IgG secondary antibody (Life Technologies, Alfortville, France). After a washing step, the oocytes were incubated for 10 min in DAPI (diluted to 1/1000) before being mounted on a slide and observed by confocal microscopy in the dark. For the spindle analysis, the oocytes with distinct and well-organized microtubules fibers associated with perfect alignment of the chromosomes at the level of the metaphase plate are identified as normal.

Stimulation and Mating of the Mice 7-week-old "young" and 7-month-old "old" B6CBAF1 females were mated with C57N males after superovulation, the latter consisting in injecting PMSG at 10 IU (Sigma-Aldrich) followed by triggering of ovulation by administration of hCG (Human Chorionic Gonadotrophin) at 10 IU (Sigma-Aldrich), 46-48 h afterwards.

The day after the mating, the mice exhibiting a vaginal plug were sacrificed. The oocytes were collected from the oviducts 15-16 h after the injection of hCG and the fertilization rate was evaluated by the presence of the second polar globule in the perivitelline space.

Incubation of the Fertilized Mouse Oocytes

The mouse oocytes fertilized after mating and collected were randomized into 4 groups (young exposed to the cyclic QDE peptide (QDEc), young controls, old exposed to QDEc, old controls) and placed in drops of culture medium (KSOM) of 20 μl for the controls, and supplemented with 100 μM of QDEc for the exposed ones. The exposure lasted from D1 to D4 after the mating in vivo (D0). The QDEc is equivalent to the human FEEc. The culture dishes are incubated at 37° C. under 5% of $CO_2$ and they are covered with mineral oil.

The oocytes were observed every day with a binocular magnifying lens in order to assess the signs of embryonic development. Normal development kinetics correspond, at a minimum, on D2, to an embryo cleaved into 2 cells and, on D5, to an embryo at the morula or blastocyst stage.

Randomized Prospective Study in Human IVF

A clinical trial was begun in the IVF laboratory of the MAP Center of Cochin, on Sep. 8, 2014, on 66 couples, the average age being 34.3±4.2 years old for the women and 37.0±5.2 for their partners. It is a randomized, single-center prospective study of in vitro fertilization (IVF) carried out in the presence or absence of FEEc. The oocytes, recovered from their cumulus, were divided up into two groups alternately into one and then into the other according to their order of recovery. When all the oocytes were recovered, a technician who had not participated in the recovery of the cumuli determined by randomization which of the two groups was inseminated in the presence of FEEc and which served as control. One part of the oocytes is incubated in the standard culture medium (Global, JCD), the other part in this same medium supplemented with 100 μM FEEc.

The methodology of this study, represented diagrammatically in FIG. 9, is presented below. Human oocytes originating from women 18 to 43 years old were recovered by ovarian puncture after hormonal stimulation by gynecologists. They were divided up in a randomized manner into 2 groups: the oocytes incubated in the presence of a standard culture medium supplemented with 100 μM FEEc or of a standard culture medium (Global, JCD), then placed in an incubator at 37° C. under an atmosphere of 5% of $CO_2$. The partner's spermatozoa were recovered in the laboratory and the most mobile selected according to a standard preparation of the MAP centers. The IVF consists in bringing the spermatozoa into contact with the oocytes in the insemination medium at a concentration of $10^5$ spermatozoa selected/ml in drops of 20 microliters under oil. The insemination is carried out in an incubator at 37° C. under 5% of $CO_2$ for 18 hours. 18 h after the insemination (D1), the corona is removed from the oocytes. The fertilized oocytes are washed and transferred into another drop of medium and placed in culture for a further 24 h. At the time of the transfer in utero, they are washed three times, then placed in a transfer medium and placed in the uterine cavity. The embryos are transferred according to their apparent quality without paying any attention to the group of origin. One or more embryos are transferred according to the age, the indication of the IVF, the attempt rank and the quality of the embryos obtained, and with the agreement of the couples. Some embryos may be placed in prolonged culture over the course of 5 days (at the blastocyst stage) either immediately, or after transfer of embryos at D2.

The main evaluation criterion is the clinical pregnancy rate by transfer of fresh or frozen embryos and the miscarriage rate taking into account the 3 groups: homogeneous transfers (controls and treated) and mixed transfers (mixture of the two).

The secondary criteria are:

The fertilization rate, i.e. the ratio of the number of zygotes having two pronuclei in the cytoplasm, 18 hours after insemination, relative to the number of ooctyes in metaphase 2 in the cohort.

The percentage of embryos of good quality, i.e. of embryos of which the cleavage sequence corresponds to the ideal sequence, that is to say: 4 to 5 cells at D2 and 8 to 9 cells at D3 and of which the blastomer fragmentation is of type A (when the volume occupied by the fragments is less than 10% of the embryonic volume) or B (when the volume occupied by the fragments is between 10% and 30% of the total volume of the embryo). Thus, these "Top" embryos correspond to the ratio of the number of embryos of each type relative to the total number of embryos for each group.

This protocol was approved by the West VI Ethics Committee on Dec. 13, 2012. The study obtained authorization from the Agence de la Biomédecine [French Biomedicine Agency] on Jul. 8, 2013. The IVF is carried out with strict adherence to good clinical practice. Each couple agreeing to participate in the study signed a free and informed consent document.

Statistical Analysis

The quantitative variables were studied by means of their numbers, mean and standard deviation. The data were compared between the exposed and non-exposed group using an appropriate test (Student's test or Wilcoxon test) for the quantitative variables. The comparisons of percentages were carried out using a Chi-squared ($\chi^2$) test or Fisher's exact test. The differences between the compared data were considered to be statistically significant when the p value (significance threshold) was less than 0.05.

Example 1: Improvement in the Spermatozoan Movement Parameters and in the Percentage of Hyperactivated Spermatozoa in Men Preliminary experiments showed that, in an 18-hour survival test of sperms incubated in the presence of the FEE peptide, the survival is significantly improved in the group treated with the FEE at the concentration of 100 μM compared with the control.

Example 1a: Automated Analysis of the Sperm Movement Parameters after Incubation in the Presence of FEEc and of a Scramble Peptide for Control The results presented in table 1 below show an increase in the smoothed VAP (p=0.008), in the VSL (p=0.048), in the VCL (p<0.0001) and in the ALH (p=0.002), resulting in a 29% increase in hyperactivated spermatozoa (p=0.009) compared with the control group. This improvement in the percentage of hyperactivated spermatozoa explains the improvement in their fusiogenic capacity and the increase in the fertilization rates recorded in mice on intact oocyte cumulus complexes.

TABLE 1

Automated analysis of sperm movement parameters compared between the control group and the group after incubation in the presence of FEEc.

| Parameters | Control | FEE | P | |
|---|---|---|---|---|
| VAP (μm/s) | 81.0 ± 16.8 | 86.3 ± 13.7 | 0.008 | 7% |
| VSL (μm/s) | 67.3 ± 16.7 | 71.8 ± 15.3 | 0.048 | 7% |
| VCL (μm/s) | 137.5 ± 26.7 | 148.0 ± 26.6 | <0.0001 | 8% |
| ALH (μm) | 6.1 ± 1.3 | 6.6 ± 1.3 | 0.002 | 8% |
| BCF (Hz) | 32.7 ± 3.4 | 33.0 ± 3.9 | NS | — |
| STR (%) | 85.8 ± 11.4 | 84.9 ± 10.0 | NS | — |
| LIN (%) | 51.1 ± 12.6 | 50.9 ± 12.2 | NS | — |
| Hyperactivation | 12.3 ± 9.7 | 15.9 ± 11.6 | 0.009 | 29% |

Example 1b: Measurement of the Mitochondrial Membrane Potential

The mitochondrial membrane potential is found to be increased by 21% in the presence of the FEEc peptide compared with the "scramble" peptide (p<0.001) (FIG. 1).

The FEEc therefore improves the sperm movement parameters by increasing the sperm mitochondrial membrane potential.

Example 1c: Study of the Fertilization Index

The results presented in FIG. 2 show that not only a larger number of spermatozoa fused with the oocytes with the pellucida removed, in the presence of the FEEc peptide, but said spermatozoa are also decondensed, contrary to those of the control group.

A mean of 19.0±4.6 spermatozoa is counted in the cytoplasm on the control oocytes, whereas an increase with 36.9±11.7 spermatozoa fused by oocytes is reported after incubation with the FEEc at 100 μM (p<0.001). This phenomenon suggests an increase in the fertilization capacity of the spermatozoa and an oocyte activation mediated by the FEEc peptide.

The sperm movement parameters of 37 patients were analyzed in the presence or absence of FEEc (incubation for 3 hours). There is a significant increase in the percentage of hyperactivated spermatozoa according to the Mortimer criteria, which explains the increase in their fertilization capacity (see table 1 above).

Example 2: Improvement in the Percentages of In Vitro Maturation of Immature Human Oocytes A significant increase in oocyte maturation with FEEc was demonstrated at D1, for all of the human oocytes tested. The results obtained are the following: 42.3% ($^{69}/_{163}$) of oocytes in metaphase II (MII) with FEEc versus 30.0% ($^{52}/_{173}$) in the control group, p=0.02 (FIG. 3). The increase in maturation is even more marked for the oocytes from women aged 37 and over as soon as D1. The results obtained are the following: 47.9% ($^{23}/_{48}$) of oocytes in MII with FEEc versus 20.4% ($^{11}/_{54}$) in the control group (p=0.003).

Although small for the oocytes from women less than 37 years old, the improvement in oocyte IVM in human beings is very significant for oocytes of older women since the same maturation rate as for the oocytes of the young women was obtained (47.9% of the oocytes in metaphase II in the presence of FEEc versus 20.4% in the control group, p=0.003).

The results obtained with the 336 human oocytes at the GV stage, incubated in randomized manner in the presence or in the absence of the FEEc peptide, show that the presence of the FEEc improves the maturation rate of human oocytes.

No significant difference between the oocyte atresia rates among the 2 groups was detected (16.5% in the presence of the peptide versus 16.8% for the control group) (FIG. 4). In the sample of women aged 37 and over, a non-significant tendency toward a decrease in the atresia rate is noted in the presence of the FEEc peptide (16.7%, $^{8}/_{48}$) compared with the control medium (24.1%, $^{13}/_{54}$) p>0.05.

The study was continued and supplementary results were obtained. These results confirm the results described above and demonstrate other effects of the FEEc peptide, as described below.

In total 600 oocytes were matured in vitro. For the analysis, only one oocyte per woman was included in the study in order for all the events to be independent. In the presence of fertilin in the medium, the maturation rate went from 38.3% to 59.0% (P<1.6×10$^{-4}$) (FIG. 12). When the analysis is carried out as a function of the age of the woman from whom the oocytes in GV originate, it is seen that the improvement in the maturation is relatively modest for women under the age of 37 (42.6% to 51.8%, P<0.2), but that it is much greater in the oocytes originating from women aged 37 and over (35.1% to 65.9%, P<3.91×10$^{-5}$). Fertilin is therefore able to stimulate the in vivo maturation of the oocyte with the corona removed, and the expulsion of the first polar globule. Apparently, the greater the age-related energy deficit of the oocyte, the better the fertilin performs this stimulation. This study also made it possible to demonstrate an increase in the maturation rate more particularly of the oocytes in GV of women over the age of 37 and under the age of 30 (FIG. 13).

Example 3: Organization of the Meiotic Spindle of Human Oocytes Matured In Vitro FIG. 5 shows the incomplete and aberrant organization of the alignment of the chromosomes on the metaphase plate with non-aligned chromosomes. The image is obtained from a human oocyte in MII after 24 h of IVM in the presence of the control medium.

Example 4: Improvement in the Rate of Fertilization and Early Embryonic Development in Mice At D1, the fertilization rate remains unchanged in the young mice, whereas it goes from 39% to 51% in the old mice (p<0.03) (FIG. 6).

At D2, among the young mice, 50.0% ($^{26}/_{52}$) of the oocytes are cleaved in the QDEc group compared with 32.4% ($^{18}/_{56}$) in the control group (P=0.02) (FIG. 7). Regarding the old mice, there are significantly more cleaved embryos at D2 in the presence of QDEc (58.7%, $^{37}/_{63}$) compared with the control (35.4%, $^{23}/_{65}$), p=0.008. At D4, the proportion of cleaved embryos from young mice that reach the morula or blastocyst stage is 34.6% ($^{7}/_{16}$) for the control group compared with 63.0% ($^{17}/_{26}$) for the medium supplemented with QDEc, p<0.03. This proportion reaches 86.3% ($^{63}/_{73}$) for the old mice in the presence of the peptide compared with 28.3% ($^{15}/_{53}$) in the control medium, p=0.001.

Advantageously, the blast formation in the mice is improved in the presence of the QDEc peptide.

The percentages of atresic embryos are not significantly different between the 2 groups among the young mice: 17.3% ($^{9}/_{52}$) in the presence of QDEc and 30.4% ($^{17}/_{56}$) for the control (p=0.1). Compared with the young mice, the percentage of atresia is greater in the group of old mice with rates similar between the QDEc (38.1%, $^{24}/_{63}$) and control (49.2%, $^{32}/_{65}$) groups (p=0.2) (FIG. 8).

In order to more finely study the preimplantation embryonic development, the following protocol was carried out: mice were mated at D0. At D1, the oocytes were recovered by laceration of the tube bulbs. They were then dispensed into two groups in randomized fashion and placed in culture with or without QDEc, before fertilization.

The results show an increase in the morulas at D3, in the blastocysts at D4 and among these an increase in the expanded blastocysts when the oocyte was incubated in the presence of QDEc (31.1% vs 45.9%, P<0.009) (FIG. 14). Furthermore, after transfer of these blastocysts into pseudogestational females, there is a significant increase in the number of progeny obtained by transferred embryos, especially for the embryos originating from young mice (table 2 below).

TABLE 2

Birth rates after transfer of the control embryos and embryos treated with QDEc in mice

| Mice | | Embryos transferred (n) | Progeny (n) | Birth rate | P |
|---|---|---|---|---|---|
| Young | Control | 109 | 37 | 34% | 0.05 |
|  | Fertilin | 132 | 61 | 46% |  |
| Old | Control | 58 | 20 | 35% | 0.61 |
|  | Fertilin | 30 | 12 | 40% |  |
| Total | Control | 167 | 57 | 34% | 0.04 |
|  | Fertilin | 162 | 73 | 46% |  |

Example 5: Increase in the Clinical Pregnancy Rates by In Vitro Fertilization

The results presented below were obtained in the context of the "fertilin" study.

In a first step, 56 couples were included. The average age is 33.9+/−4.1 years old among the women and 36.7+/−5.3 for the partners. No significant difference was noted, either between the fertilization rates or between the percentage of top-quality embryos among the 2 groups, FEEc versus control. A non-significant tendency toward increasing the pregnancy rate by transfer is noted in the presence of the peptide compared with the control and with the mixed group, 46.1% ($^{6}/_{13}$) compared with 29.4% ($^{5}/_{17}$) and 40% ($^{2}/_{5}$), respectively (FIG. 10 and table 2 below). A miscarriage was reported after transfer of one embryo from the control group. No adverse effect has been reported to date.

To date, 66 couples have been included in the study. 54 transfers were carried out, 26 with control embryos, 22 with embryos of the FEE group, 6 with embryos of the two groups (mixed transfers). The rate of cumulative pregnancy was respectively 34.6%, 45.5% and 33.3% in the 3 groups. The rate of spontaneous miscarriage was respectively 33.3%, 10% and 0%. The rate of clinical pregnancy is therefore respectively 23%, 41% and 33.3%. An essential fact when the rate of clinical pregnancy is relative to the age of the patient is that, in the young patients, it is seen that the rate of evolutive clinical pregnancy (that is to say pregnancy to term) is significantly increased from 20% to 57.1% (P<0.03).

TABLE 3

Pregnancy rate by transfer (for 66 patients)

| Embryo transfer | Control | FEEc | Mixed | Total |
|---|---|---|---|---|
| Patients included | | | | 66 |
| Deferred transfers | | | | 21 |
| Cumulative transferred | 26 | 22 | 6 | 54 |
| Pregnancy rate n (%) | 9 (34.6%) | 10 (45.5%) | 2 (33.3%) | 38.9% |
| Miscarriages n (%) | 3 (33.3%) | 1 (10.0%) | 0 | 4 (19%) |

The results also show an increase of 21% in clinical pregnancies after transfer of an embryo from the FEEc group, 40.0% (8/20) compared with 33.3% (8/24) in the control group (p>0.05). The fertilization rates are 66.2% among the controls compared with 67.6% in the group exposed to the FEEc (p>0.05). The rate of early spontaneous miscarriage reaches 37.5% (3/8) in the control group compared with 11.1% (1/9) when the embryo has been exposed to the FEEc (p>0.05) (FIG. 11).

For the women under the age of 37, after exposure to the FEEc, the fertilization rates are 70.9% compared with 68.3% in the control group. In the case where the oocyte was exposed to the FEEc, the pregnancy rates reach 57.1% compared with 20.0% in the control group (table 4 below).

TABLE 4

Fertilization rate and pregnancy rate according to age of the partner (≥37 or <37 years old)

| Woman's age (year) | Number of couples (n) | Fertilization rate Control (%) | Fertilization rate FEEc (%) | Pregnancy rate Control (%) | Pregnancy rate FEEc (%) |
|---|---|---|---|---|---|
| 26-36 | 47 | 68.3% | 70.9% | 20.0% | 57.1%* |
| 37-43 | 19 | 60.2% | 60.3% | 33.0% | 20.0% |

*P < 0.03

Of the first 66 couples included in the study up to now, 51 transfers have been carried out, the others being deferred and the results show that of these 51 transfers:

21 were carried out using embryos of the control group;

18 using the group in the presence of the FEEc;

12 with embryos of the two groups.

The pregnancy rate is higher and there are fewer miscarriages for the group in the presence of the FEEc in comparison with the other groups (33% of miscarriages compared with 9% for the embryos in the presence of FEEc) (tables 5 and 6 below).

The pregnancy rates for the young women go from 20% to 57.1% (p<0.03) in the presence of FEEc compared with the control.

TABLE 5

Pregnancy rate by transfer (for 66 patients)

| Transfer of embryos | Control | FEEc | Mixed | Total |
|---|---|---|---|---|
| Patients included | | | | 66 |
| Deferred transfers | | | | 15 |
| Transferred patients | 21 | 18 | 12 | 51 |
| Pregnancy rate n (%) | 34.6% | 45.5% | 33.3% | |
| Miscarriages n (%) | 33% | 10% | 0 | |
| Evolutive pregnancy rate (%) | 23% | 41% | 33% | |

TABLE 6

Pregnancy rate by transfer as a function of the age of the women

| Age F | Couples No. | Fertilization rate Control(%) | Fertilization rate FEE(%) | Pregnancy rate/transfer Control(%) | Pregnancy rate/transfer FEE(%) | Fisher |
|---|---|---|---|---|---|---|
| 26-36 | 47 | 68.3% | 70.9% | 20% (4/20) | 57.1% (8/14) | P = 0.03 |
| 37-43 | 19 | 60.2% | 60.3% | 33% (2/6) | 10% (1/10) | P = 0.5 |
| Total | 66 | 66.23% | 67.6% | 23% (6/26) | 37.5% (9/24) | P = 0.2 |

The continuation of the fertilin study made it possible to obtain additional results. In total, 66 couples were included in the study. The results are reported in the tables below.

The overall data of the attempts are reported in table 7. The overall fertilization rates were virtually unmodified. However, the percentage of attempts for which there was a paucity of fertilization (less than 20% fertilization rate) fell from 37.9% to 27.3% in the presence of FEEc, suggesting a better fertilization capacity of the gametes in the presence of fertilin. Likewise, the polyspermy is of the same order of magnitude in the fertilin group as in the control group (4.0% vs 5.2%) showing that the normal mechanism for blocking polyspermy was not modified.

TABLE 7

Overall results of the fertilin study on 66 patients
General data

| | Total | Control | Fertilin |
|---|---|---|---|
| No. couples | 66 | | |
| Age man | 37 ± 5.2 | | |
| Age woman | 34.3 ± 4.2 | | |
| No. oocytes | 647 | 325 | 322 |
| No. M2 | 592(91.4%) | 302(92.9%) | 290(90.0%) |
| No. 2PN | 396 | 200 | 196 |
| No. 3PN | 30 | 17 | 13 |
| Paucity of fertilization | | 25(37.9%) | 18(27.3%) |

TABLE 7-continued

Overall results of the fertilin study on 66 patients
General data

|  | Total | Control | Fertilin |
| --- | --- | --- | --- |
| Fertilization failure | 10 | 6(9.1%) | 4(6.1%) |
| Useful blast formation | 133(33.6%) | 70(35.0%) | 63(32.1%) |

The results of all the couples having had a transfer of embryos are reported in table 8. This table excludes the couples who had an unexplained fertilization failure in the 2 groups of oocytes with or without fertilin (n=6).

TABLE 8

Results obtained in the 66 couples of the fertilin study
All patients (66 couples included)

| Embryos transferred | No. ooc. | Fert. rate | Blast (%) | No. transfer Implant rate | Pregnancy n | Spont. Miscar. | Evolutive pregnancy | Weight at birth (n babies) |
| --- | --- | --- | --- | --- | --- | --- | --- | --- |
| Control | 151 | 69.5% | 37.1% | 36(39.5%) | 16 | 5(33.3%) | 11(30.5%) | (6)2951 g |
| FEEc | 98 | 78.6% (NS) | 37.7% | 34(35.1%) | 13 | 2(15.4%) | 11(32.5%) | (9)3041 g |

As shown in table 8, for the patients having had an embryo transfer, the fertilization rate went from 69.5% to 78.6%, which is an improvement of 13% but which does not reach significance in the present cohort. The embryonic development up to the blastocyst stage is not modified, nor is the rate of implantation of the embryos in the uterus. On the other hand, the rate of miscarriages is decreased by close to 50% in the fertilin group (15.4% vs 30.5%).

The results of the couples having had an embryo transfer and in which the woman is under the age of 37 are reported in table 9.

If one takes into consideration only the couples in which the woman is under the age of 37 (n=47) and which correspond to more than 70% of the patients treated, it is seen that the fertilization rate is significantly improved from 70.9% to 83.3% (P<0.05).

The rate of miscarriages goes from 36.3% for the patients having received an embryo of the control group to 9.1%, that is to say four times lower, for those having received an embryo of the fertilin group. In fact, the rate of evolutive pregnancies giving birth to a child goes from 28.6% in the group of the control embryos to 41.6% in that of the embryos of the fertilin group.

TABLE 9

Results obtained in the couples in which the woman is
under the age of 37 in the context of the fertilin study
Patients <37 years old (47 couples included)

| Embryos transferred | No. ooc. | Fert. rate | Blast (%) | No. transfer Implant rate | Pregnancy n | Spont. Miscar. | Evolutive pregnancy | Weight at birth (n babies) |
| --- | --- | --- | --- | --- | --- | --- | --- | --- |
| Control | 127 | 70.9% | 36.7% | 28(37.9%) | 12 | 4(36.3%) | 8(28.6%) | (7)2894 g |
| FEEc | 72 | 83.3% P < 0.05 | 36.7% | 24(44.0%) | 11 | 1(9.1%) | 10(41.6) | (8)3271 g |

What is claimed is:

1. A method of maturating immature mammalian oocytes in vitro comprising:
contacting the immature mammalian oocytes in vitro with at least one cyclic peptide comprising a cyclic tripeptide F-E-E of SEQ ID NO: 1 with a cyclization linkage between the two end cysteines, thereby maturating the mammalian oocytes.

2. The method of claim 1, wherein the immature mammalian oocytes are human oocytes.

3. The method of claim 1, wherein the immature mammalian oocytes are incubated with 1 to 100 μM of cyclic peptide for a period of between 1 minute and 4 days.

4. The method of claim 1, wherein contacting the immature mammalian oocytes with the cyclic peptide decreases the risks of miscarriage.

5. The method of claim 1, wherein contacting the immature mammalian oocytes with the cyclic peptide decreases the risks of aneuploidy in the oocyte.

6. The method of claim 5, wherein the aneuploidy is trisomy.

7. The method of claim 1, wherein the immature mammalian oocytes are human oocytes from a woman 37 years old or older.

8. The method of claim 1, wherein the immature mammalian oocytes are human oocytes from a woman under the age of 30.

9. The method of claim 1, wherein contacting the immature mammalian oocytes with the at least one cyclic peptide improves ploidy of oocytes.

* * * * *